(12) United States Patent
Bock et al.

(10) Patent No.: US 7,303,875 B1
(45) Date of Patent: Dec. 4, 2007

(54) NANO-CHEM-FET BASED BIOSENSORS

(75) Inventors: Larry Bock, Olivenhain, CA (US); R. Hugh Daniels, Mountain View, CA (US); Stephen Empedocles, Mountain View, CA (US)

(73) Assignee: Nanosys, Inc., Palo Alto, CA (US)

( * ) Notice: Subject to any disclaimer, the term of this patent is extended or adjusted under 35 U.S.C. 154(b) by 355 days.

(21) Appl. No.: 10/683,583

(22) Filed: Oct. 9, 2003

Related U.S. Application Data

(60) Provisional application No. 60/417,761, filed on Oct. 10, 2002.

(51) Int. Cl.
 *C12Q 1/68* (2006.01)
(52) U.S. Cl. .......................................... 435/6
(58) Field of Classification Search ...................... None
 See application file for complete search history.

(56) References Cited

U.S. PATENT DOCUMENTS

| | | | |
|---|---|---|---|
| 6,331,438 B1 | 12/2001 | Aylott et al. | |
| 6,716,620 B2 * | 4/2004 | Bashir et al. | 435/287.2 |
| 6,733,828 B2 * | 5/2004 | Chao et al. | 427/239 |
| 6,828,786 B2 | 12/2004 | Scherer et al. | |
| 2002/0117659 A1 | 8/2002 | Lieber et al. | |
| 2002/0172963 A1 | 11/2002 | Kelley et al. | |
| 2003/0102510 A1 * | 6/2003 | Lim et al. | 257/368 |
| 2004/0038307 A1 * | 2/2004 | Lee et al. | 435/7.1 |

FOREIGN PATENT DOCUMENTS

| | | |
|---|---|---|
| WO | WO 02/48701 | 6/2002 |
| WO | WO 03/085700 | 10/2003 |
| WO | WO 03/085701 | 10/2003 |

OTHER PUBLICATIONS

Cui et al., Science 293:1289-1292 (2001).*
Zhao et al., 2001, Nucleic Acids Research 29(4):955-959 (2001).*
Brand et al., Appl Microbiol Biotechnol 36(2):167-72 (1991).*
Dixon et al., (1999) "Anthrax" *NEJM* 341:815.
Owicki and Parce (1992) "Biosensors bases on the energy metabolism of living cells: The physical chemistry and cell biology of extracellular acidification" *Biosensors and Bioelectronics* 7:255-272.
Parce et al., (1989) "Detection of Cell-Affecting Agents with a Silicon Biosensor" *Science* 246:244.
Delvaux et al. (2003) "Immobilisation of glucose oxidase within metallic nanotubes arrays for application to enzyme biosensors" *Biosensors and Bioelectronics* 18: 943-951.
Tiefenauer, et al. (1997) "Towards amperometric immunosensors devices" *Biosensors & Bioelectronics* 12(3): 213-223.

* cited by examiner

*Primary Examiner*—J. Douglas Schultz
*Assistant Examiner*—Jeffrey S Lundgren
(74) *Attorney, Agent, or Firm*—Quine Intellectual Property Law Group P.C.; Andrew L. Filler

(57) ABSTRACT

Methods of detecting components of interest, e.g., nucleic acids and sugars, are provided. The methods comprise contacting one or more nanowires comprising a functional group with a sample containing the component or components of interest. In one embodiment, the functional group comprises a hairpin oligonucleotide, e.g., a hairpin that changes conformation upon binding the component of interest, e.g., a nucleic acid. The change in conformation produces a change in charge that is detected. In another embodiment, the functional group comprises an enzyme, e.g., glucose oxidase, which produces a change in pH when glucose is present in a sample.

8 Claims, 14 Drawing Sheets

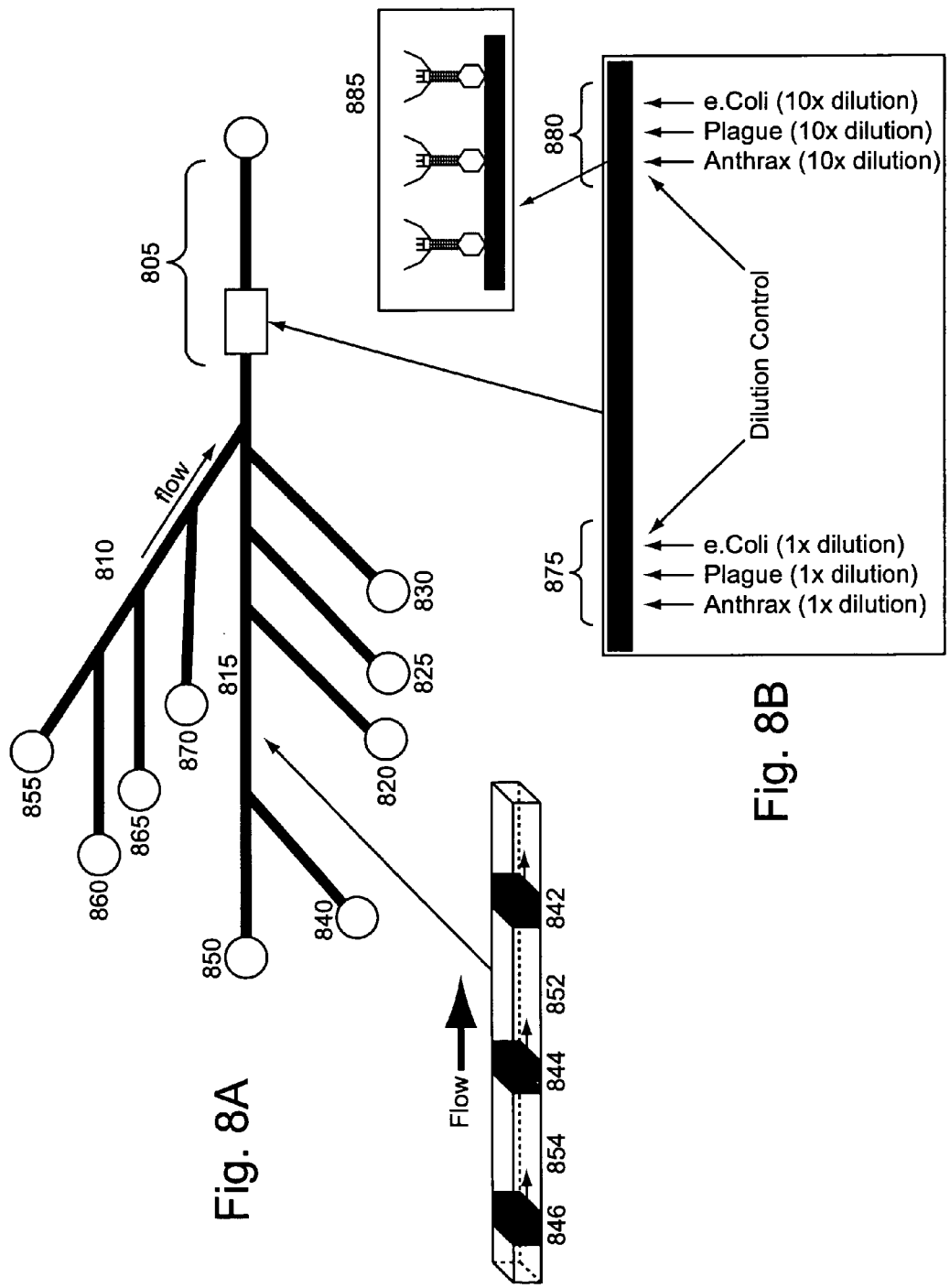

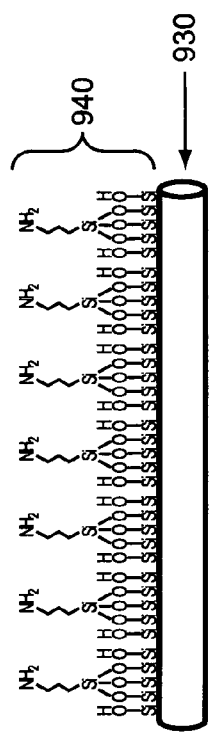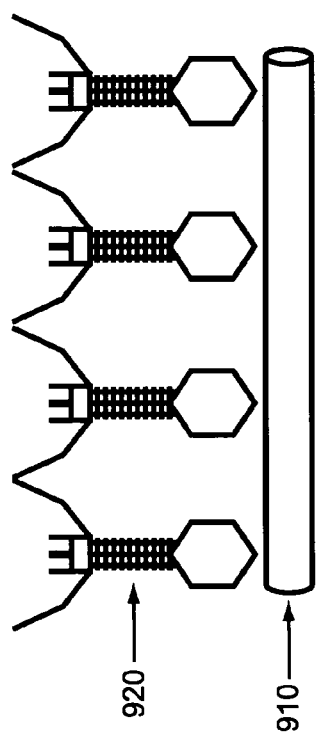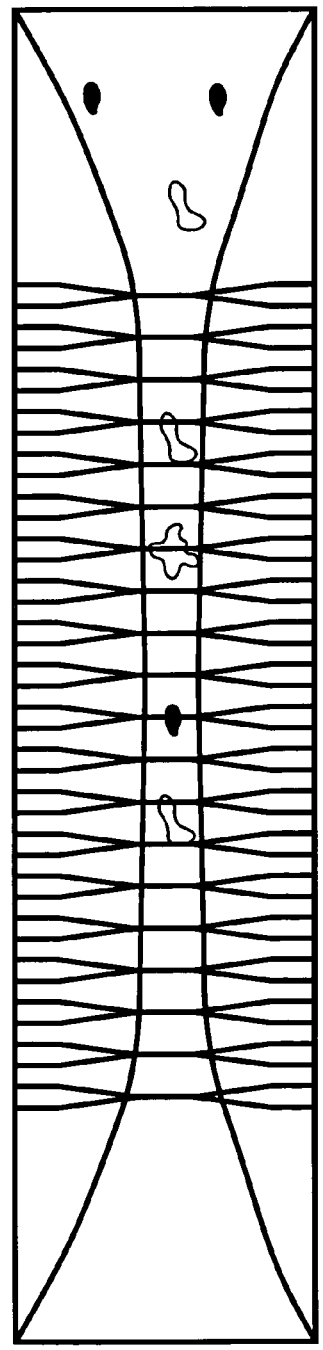
Fig. 9A
Fig. 9B
Fig. 9C

Fig. 13

NANO-CHEM-FET BASED BIOSENSORS

CROSS-REFERENCE TO RELATED APPLICATIONS

This application is a non-provisional of U.S. Ser. No. 60/417,761 "Nano-Chem-Fet Based Biosensors" by Bock et al. filed Oct. 10, 2002. The present application claims priority to and benefit of this prior provisional application, which is incorporated herein by reference for all purposes.

FIELD OF THE INVENTION

The invention is in the field of nanotechnology, including nanostructure based biosensors, including nano-chem-FET based biosensors.

BACKGROUND OF THE INVENTION

Analytical operations, particularly bioanalytical operations, have been subject to major advancements over the past thirty years, e.g., the advent of powerful analytical and manipulation techniques such as the polymerase chain reaction, recombinant DNA technology, rapid sequencing methods, and microfluidic analysis systems. However, a need still exists for greater sensitivity and specificity, higher accuracy, e.g., for kinetic analysis, greater reproducibility, and more rapid and cost-effective analytical systems.

For example, in drug discovery, large panels of molecules are often tested for their ability to modulate (e.g., inhibit or potentiate) an enzyme that is implicated in a pathological process. In addition, the ability to monitor cellular responses is important in a number of areas, such as biological research and drug discovery. For example, monitoring activity of potential anti-cancer agents and their effect on a specific cell type is critical in determining its efficacy and/or potential toxicity. Typical assays can involve incorporation and/or removal of radioactive or fluorescent labels and are time consuming, in addition to lacking sensitivity. In addition, various technologies, e.g., patch clamp, voltammetry, amperometry, fluorescence microscopy, capillary electrophoresis, e.g., with fluorescence and/or electrochemical labels, and the like, have been developed to address monitoring and detection of cellular responses and transport. However, none of the techniques is capable of real time monitoring or detection of a change in a single cell at a single molecular level. In addition, the techniques presently available do not offer a microarray format that is suitable to high throughput screening.

Furthermore, chemical sensing technologies have been developed using chemically sensitive field effect transistors, or chem-FETs, to detect the presence and/or concentration of a variety of chemical and biochemical species. These sensors employ electrical signals, as opposed to optical signals, which provide a sensitive means for detection of many analytes without the use of labels, e.g., expensive and/or potentially interfering labels. However, chem-FETs still suffer from low sensitivity.

Therefore, a need exists for a simple method that allows the detection of an analyte of interest and/or analysis of cellular behavior using a sensitive, non-invasive, label-free system that could be carried out on multiple samples in a rapid and cost-effective manner. The present invention fulfills these and other needs related to chemical, biochemical, and cellular detection.

SUMMARY OF THE INVENTION

The present invention provides nanosensors or nano-chem-FETs, e.g., comprising nanowire arrays, and methods of using them, e.g., for detection of a component of interest, a binding event, enzymatic activity, cellular detection, e.g., detection of cells, cellular events, and cellular responses, and the like. For example, nanowires and methods are provided for detection of cellular migration, cell death, a cellular response to a test compound, cell viability, and the like.

In one aspect, the present invention provides methods of detecting a component of interest, e.g., a protein, nucleic acid, enzyme, or the like. The methods typically comprise contacting a nanowire, e.g., a functionalized nanowire, with the component of interest. The component of interest interacts with, e.g., binds to, reacts with, or otherwise alters the nanowire or a functional group associated therewith, such that conductance of the nanowire changes. The change in conductance is detected, thereby detecting the component of interest.

In one embodiment, one or more nanowires comprising one or more functional groups are provided, wherein the functional group undergoes a change in charge in the presence of the component of interest. The change in charge is optionally a change in the value of the charge or a redistribution of charge. The nanowires are contacted with a test solution, e.g., a solution comprising the component to be detected. The contact results in a change in charge, e.g., change in charge value or charge distribution, which produces a signal that is detected.

For example, a nanowire functionalized with an enzymatic substrate, e.g., a protein, peptide, oligonucleotide, or the like, is optionally contacted with an enzyme that acts on the substrate, resulting in a reacted substrate having a different charge. The change in charge is detected to provide an indication of enzymatic activity. Example enzymes that are optionally analyzed with these methods include, but are not limited to, proteases, kinases, phosphatases, proteases, polymerases, transferases, ligases, and/or the like. The methods also optionally include detection and/or analysis of enzyme kinetics. For example, initial enzymatic reaction rates are optionally determined from the information detected in the above manner.

Alternatively, the functional group on the nanowire comprises a molecule that undergoes a conformational change that redistributes a charge, altering conductance of the nanowire. For example, an oligonucleotide, such as a hairpin, is optionally used to redistribute a charge moiety on a nanowire. The hairpin typically comprises a first end, a second end, and a central portion. The first end and the second end are complementary to each other and the central portion is complementary to a component of interest. In addition, the first end typically comprises a charge moiety that is proximal to the nanowires, wherein binding the component of interest to the central portion of the hairpin oligonucleotide unfolds the hairpin, thereby moving the charge moiety away from the nanowires, producing a change in charge, e.g., a charge redistribution. The change in charge produces a signal that is detected, thereby providing detection of the component of interest. Hairpin oligonucleotides are also used in this manner to provide signal amplification in a field effect transistor.

In another aspect, the present invention provides devices for and methods of detecting glucose. The devices typically comprises one or more nanowires comprising glucose oxidase immobilized thereon or proximal thereto. The methods comprise contacting the nanowires with a test solution, e.g., a solution comprising glucose. Any glucose present in the test solution is oxidized by the glucose oxidase. Oxidation of glucose results in a change in pH of the test solution, producing a signal in the nanowires, which is detected, e.g., electrically.

In another aspect, the present invention provides nanosensors and methods of measuring one or more cellular responses, e.g., a response to a test compound. The methods typically comprise contacting an array of nanowires, e.g., non-functionalized nanowires, with a plurality of cells to be tested. The cells associate with, e.g., bind to, one or more of the nanowires of the array. The proximity of the cell to the nanowire generates a first signal, which is detected. The cells are then contacted with the test compound, thereby producing one or more cellular responses. The cellular responses produce a second signal in the nanosensor, which is also detected. A comparison of the first and second signal is typically used to analyze the response of the cells to the test compound. Cellular responses analyzed in this manner include, but are not limited to, cell death, cell proliferation, cell migration, morphological changes, changes in an analyte within the cells, changes in pH, changes in membrane potential, changes in redox potential, changes in ion concentrations, and/or the like.

In some embodiments, multiple cellular responses are measured simultaneously. A signal related to the presence of cells is detected and then a test compound is added to the cells, which causes one or more responses. For example, monitoring the entire array yields information on a number of cellular responses simultaneously. Cell death is detected by loss of signal in a particular area of the array, e.g., due to cells dissociating from the nanowires. Cell migration is measured by a shift in signal to a different portion of the array. Cell proliferation is measured as an increased signal in a specific area of the array, e.g., due to additional cells associating with the nanowires of the array.

In another aspect, intracellular detection devices and methods are provided, e.g., to measure a cellular response to a test compound such as a drug, a toxin, a pathogen, a virus, an enzymatic inhibitor, an enzymatic activator, or the like, or to measure a membrane potential. The methods typically comprise positioning a nanowire such that it penetrates the cellular membrane. For example, cells can engulf a nanowire via endocytosis, e.g., by depositing the cells on a nanowire. The nanowire is typically positioned such that a signal is generated in the nanowire in response to the cellular response, e.g., a change in an analyte within the cell, a change in pH, a change in a membrane potential, a change in a redox potential, a change in an ion concentration, or the like. The signal is then detected, providing a measure of the cellular response. In other embodiments, a membrane potential is measured using a nanowire that is positioned proximal to a cellular membrane, e.g., using a microwell with a liquid-tight seal.

In another aspect, the present invention provides devices and methods of detecting the presence of a component of interest, e.g., a cell, and/or a cellular event, separately or simultaneously. Devices used typically comprise a nanosensor array comprising a plurality of functionalized nanowires for detecting the component of interest and a plurality of non-functionalized nanowires, e.g., for detecting the cellular event. Example functionalized nanowires include, but are not limited to, nanowires comprising a phage or antibody capture or ligand molecule. The arrays are contacted with a test solution comprising one or more component of interest. The component of interest binds to, or otherwise associates with, the functionalized nanowires, resulting in a first signal and a cellular event. The cellular event results in a second signal, e.g., in the non-functionalized nanowires. Both signals are detected, thereby detecting the presence of the component of interest and the cellular event. For example, a cellular event is optionally cell growth or cell death. In some embodiments, cell viability is measured when the cells are detected.

In another aspect, the present invention provides methods and devices for detecting one or more cellular components, e.g., using pyrolysis. The methods typically comprise heating one or more cells and/or spores, e.g., with a cell disruption agent such as a surfactant, to fragment the cells. Cellular fragments are optionally filtered, separated, and/or condensed, e.g., prior to deposition on the nanowires. The fragmented and/or processed cells are deposited on nanowires, e.g., functionalized nanowires having a surface treated to include chemical or biochemical moieties that bind to or otherwise interact with the cellular fragments of interest. Once deposited on the nanowires, the cellular fragments are detected, e.g., due to a change in conductance in the nanowire upon binding of one or more cellular fragments. For example, specific cells or spores are optionally detected by identifying a pattern of cellular fragments.

In another aspect, the present invention provides an apparatus for analyzing cells. The apparatus typically comprises a pyrolysis chamber for fragmenting cells and a gas intake coupled to the pyrolysis chamber for introducing a gas into the chamber. A nanosensor, e.g., an array of nanowires, is typically coupled to the pyrolysis chamber for receiving fragmented cells from the pyrolysis chamber. A detector is coupled to the nanowires for detecting the fragmented cells. One or more processing stations, e.g., a separation device, a filtration device, a condenser, or the like, are also optionally coupled to the pyrolysis chamber and to the one or more nanowires for processing cellular fragments prior to detection.

Integrated detection systems for detection of cellular responses are also provided. For example, a nanosensor for use, e.g., in any of the above-described methods, optionally comprises a plurality of microwells or microchannels. One or more nanowires, e.g., an array of nanowires, is typically positioned within each of the plurality of microwells or microchannels. Cells to be tested are optionally placed into the microwells or microchannels and a detector, e.g., an electrical detector, is coupled to the nanowires for detecting one or more signals, e.g., a change in conductance of the nanowires in the array. In some embodiments, the microwells comprise a liquid tight seal, e.g., to facilitate membrane potential studies.

In another aspect, the present invention provides methods of preparing a functionalized nanowire array. The methods typically comprise providing a plurality of nanowires, e.g., suspended nanowires or nanowires in a microwell, and depositing, e.g., by pin-printing or ink-jet printing, a functional element, e.g., a hairpin oligonucleotide, an enzyme, an enzyme substrate, a protein, or the like, on the nanowires, thereby functionalizing the nanowires.

In another aspect, the present invention provides devices and methods of detecting an analyte at multiple concentrations, e.g., to provide greater dynamic range. The devices typically comprise a microfluidic device with one or more microfluidic channels disposed therein. At least a first microfluidic channel comprises a top surface and a bottom surface, wherein the top surface comprises a rough surface to aid mixing and the bottom surface comprises a nanowire array for detection. The array of nanowires is configured to detect the analyte at a plurality of positions along the bottom of the channel. The methods typically comprise flowing a buffer solution along the top of the channel and flowing a test solution comprising the analyte along the bottom of the channel. The test solution and the buffer solution mix in the channel, resulting in a concentration gradient of the analyte along the bottom of the channel. The analyte is detected at one or more of the plurality of positions along the bottom of the channel, thereby detecting the analyte at multiple concentrations. This method is also used to detect a cellular response, e.g., at multiple concentrations of a test compound, or, e.g., alternatively, to detect the presence of cells.

In another aspect, the present invention provides a method of amplifying a field effect signal. The method comprises providing a field effect transistor comprising a substrate and linking molecule to the nanowire, which molecule is capable of redistributing a charge moiety. For example, a redistribution molecule is a molecule that undergoes a conformational change to redistribute a charge moiety in a manner that alters the relative effect of the charge moiety on the nanowire. A typical redistribution molecule of the invention is an oligonucleotide, e.g., a hairpin oligonucleotide, that undergoes a conformational change, e.g., upon binding to another molecule. As described above, a hairpin typically comprises first and second complementary ends and a central portion. The central portion is complementary to a component of interest and the first end typically comprises a charge moiety, e.g., a latex bead comprising a carboxylate or amine surface, a nucleic acid, one or more negatively charged nucleotides, a highly charged polypeptide, a charged polymer, a charged oligonucleotide, polyarginine, histidine, lysine, or any other large charged molecule, or a metal nanocrystal, proximal to the substrate. The component of interest binds to the central portion of the hairpin oligonucleotide resulting in a signal and unfolding the hairpin. When the hairpin unfolds, the charge moiety is moved away from the substrate and amplifies the signal.

In another aspect, the present invention provides methods of analyzing binding events, e.g., by fluctuation analysis. The methods typically comprise contacting a nanowire with one or more components of interest, which components of interest bind to the nanowire. Contact between the nanowire and the component of interest results in a plurality of binding events, wherein each of the binding events produces a signal, e.g., a fluctuation in a signal. The signal is detected and fluctuations in the signal are analyzed to provide information on the binding event.

BRIEF DESCRIPTION OF THE DRAWINGS

FIG. 8A provides an example configuration for a microfluidic system used in conjunction with a nanosensor.

FIG. 8B provides an example of multiple array capture fields in a single channel, e.g., for detection of multiple components, e.g., at multiple concentrations.

FIG. 9A is a schematic of a phage functionalized nanowire.

FIG. 9B provides an illustration of a pH sensing nanowire.

FIG. 9C illustrates fluid flow over a nanowire array positioned within a microchannel.

FIG. 13 provides a schematic of bacterial fingerprinting techniques utilizing nanowires.

DETAILED DESCRIPTION

Figure 1:
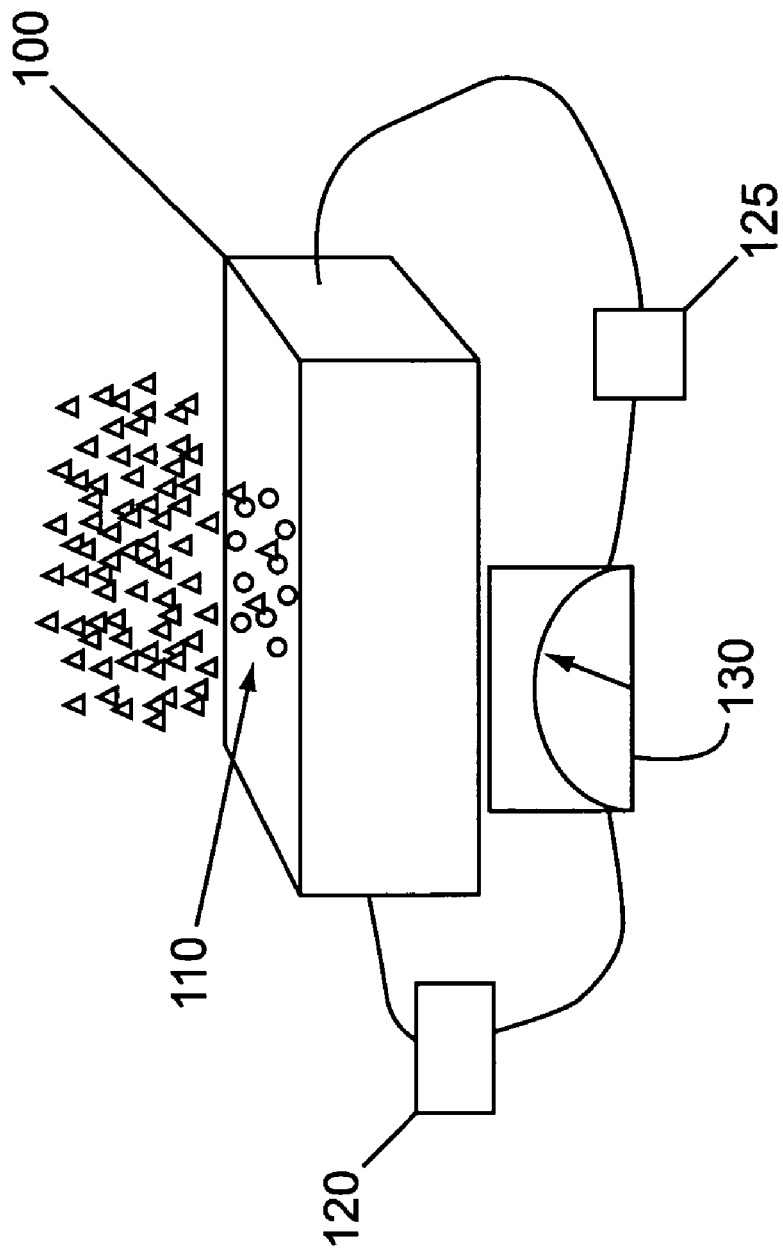
FIG. 1 provides a schematic illustration of a standard field effect transistor.

The present invention provides biosensors, e.g., nano-chem-FET based sensors, and methods of using them, e.g., for detection of a component of interest, detection of a change in charge or pH, detection of a cellular event or cellular response, or the like. For example, nanosensors and methods are provided for measurement of enzymatic activity, detection of glucose, detection of cellular migration and/or cell death, and the like.

The nanosensors of the invention, e.g., comprising nanowires or other nanostructures and/or nanostructure (e.g., nanowire) arrays, are of extremely small dimension such that they provide high sensitivity, high specificity, e.g., with an appropriate functional group attached, and versatility for integration into various systems e.g., due to simple electrical detection, such as microfluidic systems. In addition, the sensors provided are typically label free and uniquely suitable for in situ monitoring and detecting of chemical and/or physiological changes around a cell. For example, the sensors of the invention are optionally combined with microwell technology to provide systems and devices, e.g., for detection of a wide variety of biological pathogens simultaneously, e.g., with real time and/or continuous detection, for high speed target discovery, drug screening, and the like.

Detection of a component of interest, e.g., a cell, an analyte, a spore, an enzyme, glucose, a protein, a nucleic acid, and/or the like, with a nanosensor, typically comprises use of a functionalized nanowire or other nanostructure, e.g., a nanowire comprising a binding moiety which binds to the component of interest. When a test solution comprising the component of interest contacts the nanowire the component of interest binds to the binding moiety, resulting in a change in conductance of the nanowire. The change in conductance of the nanowire is measured, thereby detecting the component of interest. This method provides for extremely sensitive detection, e.g., detection of a single binding event.

In addition to detecting binding events, nanosensors are also optionally used to detect changes in charge and/or cellular events as described below. For example, the nanosensors provided are optionally used to measure cell viability by detecting a change in pH due to cellular metabolism.

Typically, the detectors of the invention are at least one of at least two types: nanowires that detect binding events, and nanowires/structures that detect a change in the local environment, e.g., a pH or charge change. These two types are optionally used separately or in combination to provide multi-stage detection, e.g., detection of cells combined with viability testing.

The following detailed description provides general information regarding nanosensors, e.g., how they are formed, functionalized, used for detection, and fabricated into arrays. This is followed by a description of various assays that are optionally carried out with the nanosensors and nanoarrays of the invention. Detection of components of interest by detection of changes in charge, and/or changes in pH are described followed by a description of the use of pyrolysis to detect cellular fragments, and methods of detecting analytes at multiple concentrations. The description concludes with descriptions of cellular assays, including multi-stage detection schemes, membrane potential measurements, and the like.

I. Nanosensors

Chem-FETs are field effect transistors in which the current through the transistor is modulated by the electric field generated in the presence of chemical or biological molecules bound to the surface of the transistor. One drawback of this technique is low sensitivity. The present invention provides methods and devices to overcome that drawback.

A diagram of a standard chem-FET is provided in FIG. 1. Substrate 100 typically has a functional group associated therewith, e.g., in binding assay region 110. Battery 120, resistor 125, and current meter 130 are used to provide a voltage across substrate 100. A biological sample is then added to the surface, which sample reacts with or binds to a functional group in binding assay region 110, causing a change in the electric field. The change generates a change in conductance of the substrate, which change provides a detectable signal, e.g., an electrical signal such as a change in current or voltage, e.g., as measured with current meter 130.

The concept of a nano-chem-FET, e.g., a nanosensor, is analogous to that of a standard chem-FET except that the bulk semiconductor is replaced by a nanostructure, e.g., a nanowire. The smaller size of a nanowire, e.g., smaller cross-section, provides an advantage over traditional chem-FETs because the field effect from a binding event, e.g., a single binding event, affects a much greater percentage of the conductive element, e.g., the nanowire, providing a more pronounced signal. By removing the effect of the binding from the surface of the substrate to the entire substrate, the sensitivity is increased in a nano-chem-FET. Nano-chem-FETs rely on this to provide high sensitivity detection by providing nanoscale FETs, e.g., a semiconductor nanowire, in which the entire substrate is affected by a binding event. Due to the extreme surface to volume ratio of nanowires, when molecules bind to the surface of the wire, any disruption in electron flow through the materials extends all the way through the wire. The result is that even single binding events produce large changes in the conductance of a nanowire, making a nano-chem-FET an extremely sensitive detection device. Furthermore, even close contact of a relatively large structure, such as a cell, with a nanowire causes a major effect even if that contact is not through a specific molecular binding event. The present invention provides nano-chem-FET devices and methods for detection of components of interest, e.g., cells, in addition to cellular responses such as pH changes, and/or the like.

A. Nanostructures

A "nanostructure" is a structure having at least one region or characteristic dimension with a dimension of less than about 500 nm, e.g., less than about 200 nm, less than about 100 nm, less than about 50 nm, or even less than about 20 nm. Typically, the region or characteristic dimension will be along the smallest axis of the structure. Examples of such structures include nanowires, nanorods, nanotubes, branched nanowires, nanotetrapods, nanocrystals, nanodots, quantum dots, nanoparticles, and the like.

Typically, the nanostructures of the present invention are used as a substrate material for a field effect transistor (FET), and are therefore fabricated from semiconductor materials. A typical nanostructure for use in a nano-chem-FET is a nanowire. Although the devices and methods are described below in terms of nanowires, other nanostrucures are also optionally used.

Nanostructures are often described or classified by an aspect ratio. An "aspect ratio" is the length of a first axis of a nanostructure divided by the average of the lengths of the second and third axes of the nanostructure, where the second and third axes are the two axes whose lengths are most nearly equal each other. For example, the aspect ratio for a perfect rod would be the length of its long axis divided by the diameter of a cross-section perpendicular to (normal to) the long axis.

A "nanowire" is a nanostructure that has one principle axis that is longer than the other two principle axes. Consequently, a nanowire has an aspect ratio greater than one; nanowires of this invention have an aspect ratio greater than about 1.5 or greater than about 2. Short nanowires, sometimes referred to as nanorods, typically have an aspect ratio between about 1.5 and about 20. Longer nanowires have an aspect ratio greater than about 20, greater than about 50, or greater than about 100, or even greater than about 10,000. The diameter of a nanowire is typically less than about 500 nm, preferably less than about 200 nm, more preferably less than about 150 nm, and most preferably less than about 100 nm, about 50 nm, or about 25 nm, or even less than about 10 nm or about 5 nm. The "diameter of a nanowire" refers to the diameter of a cross-section normal to the major principle axis (i.e., the long axis) of the nanowire. Where the cross-section is not circular, the diameter is the average of the major and minor axes of that cross-section. The nanowires of this invention can be substantially homogeneous in material properties, or in certain embodiments can be heterogeneous. The nanowires are optionally fabricated from essentially any convenient material or materials, but are typically semiconductor materials, e.g., doped semiconductor materials. Nanowires can have a variable diameter or can have a substantially uniform diameter, that is, a diameter that shows a variance less than about 20% (e.g., less than about 10%, less than about 5%, or less than about 1%) over the region of greatest variability and over a linear dimension of at least 5 nm (e.g., at least 10 nm, at least 20 nm, or at least 50 nm). Typically the diameter is evaluated away from the ends of the nanowire (e.g. over the central 20%, 40%, 50%, or 80% of the nanowire). A "branched nanowire" is a nanostructure having three or more arms, where each arm typically has the characteristics of a nanowire. For example, each arm can have dimensions typical of a nanowire. A branched nanowire can be substantially homogenous in material properties or can be heterogeneous. Nanowires according to this invention can expressly exclude carbon nanotubes, and, in certain embodiments, optionally exclude "whiskers" or "nanowhiskers", particularly whiskers having a diameter greater than 100 nm, or greater than about 200 nm.

The nanowires or other nanostructures of the invention typically comprise a semiconducting material, for example a material comprising a first element selected from group 2 or from group 12 of the periodic table and a second element selected from group 16 (e.g., ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from group 13 and a second element selected from group 15 (e.g., GaN, GaP, GaAs, GaSb, InN, InP, InAs, InSb, and like materials); a material comprising a group 14 element (Ge, Si, and like materials); a material such as PbS, PbSe, PbTe, AlS, AlP, and AlSb; or an alloy or a mixture thereof. Reference to the groups of the periodic table of the elements is to the new RUPAC system for numbering element groups, as set forth in the Handbook of Chemistry and Physics, 80th Edition (CRC Press, 2000). Typical materials are those from Groups III-V, II-VI, and Group IV semiconductors. For example, a p-doped crystalline silicon with a native oxide layer or a nitride layer are optionally used.

B. Synthesis of Nanostructures

Nanostructures are optionally fabricated and their size controlled by any of a number of convenient methods that can be adapted to a plurality of different materials. For example, synthesis of nanocrystals of various composition is described, e.g., in Peng et al. (2000) "Shape control of CdSe nanocrystals" *Nature* 404, 59-61; Puntes et al. (2001) "Colloidal nanocrystal shape and size control: The case of cobalt" *Science* 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 5,505,928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Growth of nanowires having various aspect ratios, including nanowires with controlled diameters, is described in, e.g., Gudiksen et al. (2000) "Diameter-selective synthesis of semiconductor nanowires" *J. Am. Chem. Soc.* 122, 8801-8802; Cui et al. (2001) "Diameter-controlled synthesis of single-crystal silicon nanowires" *Appl. Phys. Lett.* 78, 2214-2216; Gudiksen et al. (2001) "Synthetic control of the diameter and length of single crystal semiconductor nanowires" *J. Phys. Chem. B* 105,4062-4064; Morales et al. (1998) "A laser ablation method for the synthesis of crystalline semiconductor nanowires" *Science* 279, 208-211; Duan et al. (2000) "General synthesis of compound semiconductor nanowires" *Adv. Mater.* 12, 298-302; Cui et al. (2000) "Doping and electrical transport in silicon nanowires" *J. Phys. Chem. B* 104, 5213-5216; Peng et al. (2000) "Shape control of CdSe nanocrystals" *Nature* 404, 59-61; Puntes et al. (2001) "Colloidal nanocrystal shape and size control: The case of cobalt" *Science* 291, 2115-2117; U.S. Pat. No. 6,306,736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; and published PCT application WO 02/17362 by Lieber. Additional methods involving molecular lithography are also being developed for the construction of conducting nanowires and nanoparticles. See, e.g., Keren et al. (2002) "Sequence-specific molecular lithography on single DNA molecules" *Science* 297 72-75."

Growth of branched nanowires (e.g., nanotetrapods, tripods, and branched tetrapods) is described in, e.g., Jun et al. (2001) "Controlled synthesis of multi-armed CdS nanorod architectures using monosurfactant system" *J. Am. Chem. Soc.* 123, 5150-5151; and Manna et al. (2000) "*Synthesis of Soluble and Processable Rod-, Arrow-, Teardrop-, and Tetrapod-Shaped CdSe Nanocrystals*" *J. Am. Chem. Soc.* 122, 12700-12706.

Synthesis of nanoparticles is described in, e.g., U.S. Pat. No. 5,690,807 to Clark Jr. et al. (Nov. 25, 1997) entitled "Method for producing semiconductor particles"; U.S. Pat. No. 6,136,156 to El-Shall, et al. (Oct. 24, 2000) entitled "Nanoparticles of silicon oxide alloys"; and U.S. Pat. No. 6,413,489 to Ying et al. (Jul. 2, 2002) entitled "Synthesis of nanometer-sized particles by reverse micelle mediated techniques." Synthesis of nanoparticles is also described in the above citations for growth of nanocrystals, nanowires, and branched nanowires, where the resulting nanostructures have an aspect ratio less than about 1.5.

Synthesis of core-shell nanostructure heterostructures, namely nanocrystal and nanowire (e.g., nanorod) core-shell heterostructures, are described in, e.g., Peng et al. (1997) "Epitaxial growth of highly luminescent CdSe/CdS core/shell nanocrystals with photostability and electronic accessibility" *J. Am. Chem. Soc.* 119, 7019-7029; Dabbousi et al. (1997) "(CdSe)ZnS core-shell quantum dots: Synthesis and characterization of a size series of highly luminescent nanocrysallites" *J. Phys. Chem. B* 101, 9463-9475; and Manna et al. (2002) "*Epitaxial growth and photochemical annealing of graded CdS/ZnS shells on colloidal CdSe nanorods*" *J. Am. Chem. Soc.* 124, 7136-7145. Similar approaches can be applied to growth of other core-shell nanostructures.

Growth of nanowire heterostructures in which the different materials are distributed at different locations along the long axis of the nanowire is described in, e.g., Gudiksen et al. (2002) "Growth of nanowire superlattice structures for nanoscale photonics and electronics" *Nature* 415, 617-620; Bjork et al. (2002) "One-dimensional steeplechase for electrons realized" *Nano Letters* 2, 86-90; Wu et al. (2002) "Block-by-block growth of single-crystalline Si/SiGe superlattice nanowires" *Nano Letters* 2, 83-86; and U.S. patent application 60/370,095 (Apr. 2, 2002) to Empedocles entitled "Nanowire heterostructures for encoding information." Similar approaches can be applied to growth of other heterostructures.

A liquid crystalline polymer or other polymeric or small molecule matrix is optionally used to orient nanowires. Other methods for orienting nanowires are known to those of skill in the art. Liquid crystal phases of nanowires (e.g., nanorods) are described in, for example, Li et al (2002) "Semiconductor nanorod liquid crystals" Nano Letters 2: 557-560. Nanorods aligned along the stretching direction in stretched polymer films are described in e.g. Peng et al (2000) "Shape control of CdSe nanocrystals" Nature 404: 59-61. The phrase "substantially nonrandom," used to describe the orientation of nanowires, means that the nanowires do not occupy a purely random distribution of orientations with respect to each other. A collection of nanowires is substantially nonrandomly oriented if, when the position of each nanowire is represented as a vector of unit length in a three-dimensional rectangular coordinate system, at least one component of the vector average of the nanowires' orientations is non-zero (when representing a nanowire by a vector, any intrinsic difference between the two ends of the nanowire can typically be ignored). For example, the nanowires in a collection of nanowires (e.g., the nanowires in a composite material comprising nanowires) would have substantially nonrandom orientations if a higher percentage of the nanowires pointed in one direction (or in one of at least two specific directions) than in any other direction (e.g., if at least 10%, at least 50%, at least 75%, or at least 90% of the nanowires pointed in a particular direction). As another example, nanowires in a thin film of a composite comprising nanowires would be substantially nonrandomly oriented if a majority of the nanowires had their long axes more nearly perpendicular than parallel to a surface of the film (or vice versa). The preceding examples are for illustration only; a collection of nanowires could possess less order than these examples yet still be substantially nonrandomly oriented.

C. Functionalization of Nanowires

The surface properties of the nanostructures provided herein are easily modified, e.g., functionalized, e.g., using silane chemistry for silicon nanowires or other methods known to those of skill. For example, semiconductors, e.g., nanowires are optionally functionalized or derivatized with virtually any potential chemical or biological molecular recognition unit, making the wires themselves analyte independent, i.e., a nanowire array can be used for many potential applications depending what functional group is linked thereto. The nanostructures typically transduce a chemical binding event on their surface into a change in conductance of the nanowire in an extremely sensitive, real time and quantitative fashion. In fact, the sensors are optionally electronically gated to respond to the binding of a single molecule, e.g., a nucleic acid, protein, ion, or the like. For more information of the preparation of and use of functionalized nanowires, see, e.g., published PCT application, WO 02/48701 entitled "Nanosensors."

A "functionalized nanowire" or "derivatized nanowire" of the invention is one that has a functional group or ligand linked thereto. A "functional group" as used herein refers to any chemical or biological molecule or portion thereof that is linked to, or otherwise associated with, a nanowire. Typically, the functional group binds to or reacts with an analyte or component of interest. The "functional groups" of the invention typically have an affinity for and are capable of binding to at least a portion of a nanostructure's surface. Examples include, but are not limited to, biomolecules, ions, organisms, cells, surfactants, and/or the like. In addition to binding to the surface of the nanostructure, a functional group also typically interacts with a sample material or component thereof, e.g., by binding to or reacting with a component of interest. For example, functional groups include, but are not limited to, amines, antibodies, proteins, peptides, amino acids, nucleic acids, oligonucleotides, nucleotides, nucleosides, nucleoproteins, cells, bacteria, phage, antibodies, enzymes, receptors, carbohydrates, sugars, lipids, drugs, toxins, pathogens, organelles, genes, or the like. A typical functional group used to functionalize a nanowire is a binding moiety that specifically binds to a component of interest.

The phrase "specifically binds" to a component of interest refers to a binding reaction that is determinative of the presence of the component of interest in a heterogeneous solution, e.g., a sample solution such as a blood sample. Thus when a binding moiety or functional group specific to a component of interest, e.g., a protein or nucleic acid, binds to that component it binds to that particular component preferentially, e.g., out of a complex mixture of components. For example, it binds at least two times the background signal in the system, more typically 10 to 100 times background, and does not substantially bind in significant amounts to other components in the sample.

A "non-functionalized nanowire" of the invention is one that has its native surface or an unaltered oxide or nitride layer without any specific or non-specific binding moieties separately attached thereto. Typically, it does not specifically interact with, e.g., bind to or react with, any particular component. However, non-functionalized nanowires do interact with various components, although they do not do so specifically. For example, cells associate with nanowires in some embodiments, but do not specifically bind to a particular component on the nanowire. The cell is merely located within the vicinity of the nanowire, e.g., proximal thereto, such that it affects the electric field of the nanowire. In this case, all cells in a mixture would associate with the nanowire in essentially the same manner.

Nanowires are optionally functionalized or derivatized prior to assembly into an array or device or after such assembly. For example, the present invention provides methods of functionalizing nanowires after assembly to avoid the problems associated with surface conjugation prior to assembly, e.g., exposure of the functional group to high temperatures used in general assembly of a nanowire array. The methods typically comprise placing a small drop, e.g., about 1 to about 10 microliters, over the location of a wire. The functional group becomes conjugated or linked to the wire, thereby functionalizing the wire.

Alternatively, the functional group is simply placed in the vicinity of the nanowire and is optionally not physically linked to the surface of the nanowire. For example, an array of nanowires in a microchannel or on a substrate of some other type, e.g., a microwell or a silicon substrate are optionally functionalized by placing a drop of a solution comprising the functional group over the area in which the nanowires are located. The nanowires and the surface substrate are optionally functionalized when the surface chemistry of the nanowire and the surface are the same, e.g., $SiO_2$. and both contain a chemical element with an appropriate binding element for the functional group, e.g., a silane. Alternatively, the wire and the surface have different chemistries, allowing the wire or substrate to be functionalized separately.

The solution and/or gas used to functionalize the nanowires of the invention is optionally deposited onto the wires using the same techniques that are typically used for DNA array spotting, e.g., pin printing or ink-jet printing. The volume of solution used and the placement of the solution are optionally selected to cover one or more wires simultaneously. Multiple wires are optionally spotted with different chemistries or immersed in different chemistries, e.g., using different solutions to provide different functional groups on different wires. For example, the wires are optionally multiplexed to provide arrays comprising multiple functional groups, e.g., binding moieties for providing a bacterial fingerprint. In some applications, a functional group does not need to be linked to or localized to the wire. For example, large analytes such as cells need only be near the wire to establish a signal.

For example, a functionalized array of nanowires is optionally created by positioning an array of electrodes that each have nanowires between them and then depositing a functionalizing agent over the electrode to create a functionalized nanowire. In some embodiments, nanowire array kits are provided wherein an array of electrodes and nanowires is provided with one or more solutions for functionalizing the nanowires, e.g., when ready to use.

D. Generation of and Detection of a Signal in a Nanosensor

Biosensors are analytical devices that convert molecular events into electrical signals, e.g., without the use of labels to chemically enhance detection. The nanosensors of the invention are typically used to detect components of interest, cellular responses and events, and/or the like. Detection is possible because binding events, changes in environment, e.g., pH, changes in charge, and the like affect the electric field of the nanostructure substrate, e.g., the nanowire, producing a signal. A "signal" as used herein refers to a detectable change in a nanowire. Typically, the detectable change is a change in conductance of the nanowire. The signal is also optionally expressed in terms of a change in the voltage across the nanowire, or the current through the nanowire. Such changes are typically detected electrically, e.g., with a voltmeter and/or a current meter. Alternatively, the signal is detected digitally.

Typically, a voltage is applied across a nano-chem-FET substrate, e.g., a nanowire, providing a steady state signal. When a binding event occurs on the substrate, the electric field in the vicinity of the nanowire changes and the conductance of the nanowire changes, producing a fluctuation or shift in the steady state signal. The signal is detected, electrically or digitally, and provides real time detection of the event of interest. The present invention relies on the generation of the signal to detect various components of interest, changes in pH, changes in membrane potential, changes in charge, and the like, as described below. In addition, the invention provides improved methods of detection, e.g., methods of amplifying FET signals, methods of increasing the dynamic range of a FET signal, and methods of analyzing the signals. These methods are described in more detail below.

The temporal resolution of a nano-chem-FET is faster than the time scale of most biologically relevant molecular events, which typically require microseconds of time to occur. In addition, the small sensing surface area of a nanosensor, e.g., about 0.1 to about 10 μm overcomes the spatial limitation of most presently available biosensors.

Although described below in terms of binding events, other molecular events are also detectable as described, e.g., change in charge. Each bound molecule contributes a signal to a biosensor that approximates a step-function change in the signal for the duration of the binding event, and single molecule detection requires the detection of such step function changes. The nanowires presented herein are typically used to detect these changes. To do so, the sensors typically discriminate between single molecule changes in signal from other variations in signal, e.g., noise and binding and unbinding of other molecules. Because noise in a sensor typically correlates positively with surface area, the nanosensors presented herein exhibit low noise, while at the same time having high enough sensitivity to detect a single molecular event.

Fluctuation analysis is optionally used, e.g., to analyze single molecular events in an overlapping signal generated from a plurality of molecular events. Fluctuation analysis makes use of the fluctuations in a signal having a steady state average with very small fluctuations. The fluctuations correspond to overlapping binding and unbinding events. The ratio of the fluctuation intensity to average signal is approximately proportional to the reciprocal square root of the average number of bound molecules. Since any signal inherently carries its own noise, the noise in the average signal (not due to binding events) can swamp the fluctuations in signal due to binding events. Therefore, a small number of binding events is beneficial. The small size of the nanosensors provided herein have an advantage in this regard.

The following description distinguishes between two types of single molecule detection. The first type occurs when exactly one molecule is detected in a unique event. This represents extremely sensitive detection. The second type is when many different single molecule events are detected, providing a statistically robust estimate of the properties of the sample. For example, detection of a single molecule provides little information regarding concentration of a sample, wherein repeated detection of the single molecule can give a precise estimate of the concentration. In addition, there is additional information about the identity and functional behavior of a molecule, e.g., equilibrium constants and kinetic data, that can be obtained with statistical analysis of fluctuations in a signal.

A convenient way to do this is to record a sensor signal as a function of time, under conditions in which many single-molecule events are contained within the record. For example, the number of molecules bound to a sensor might fluctuate around equilibrium, with each binding event having an amplitude and duration obeying appropriate statistical laws. The extraction of information about the sample is optionally obtained by a statistical analysis of the fluctuations in the recorded signal. For example, this type of fluctuation analysis has been used in single channel recording in electrophysiology, e.g., for patch clamp assays, and in fluorescence fluctuation spectroscopy. Nanosensors as provided herein do not require the use of labels as in fluorescence spectroscopy and are not as invasive as patch clamp assays and therefore provide advantages over both of these methods. However, similar analytical methods are optionally used.

For example, patch clamp assays used in electrophysiology permit the detection of ion currents through gated single ion channels in biological membranes. This is a very different from a nanosensor, such as a nano-chem-FET, in terms of physical principles of the sensor, even though nanosensors are optionally used to measure potential across the membrane as the patch clamp assays do. Nevertheless, there are similarities in the analysis of the resulting fluctuation data. For example, a correspondence exists between the mean current through an ion channel and the mean change in a nano-chem-FET signal when a binding event occurs. Likewise, the rate constant for an ion channel transition from closed to open state and the rate constant for molecular binding to a nano-chem-FET are similarly comparable.

Similarly, the rate constant for the ion channel transition from open to closed state can be compared to the molecular dissociation constant for a nano-chem-FET.

Typically, in fluorescence spectroscopy, a laser beam is tightly focused to a volume of about a femtoliter in a confocal optical detection instrument. The average number of molecules in such a volume can be very small, e.g., 0.6 molecules per femtoliter (about 1 nanomolar). As fluorescent molecules diffuse into and out of the focused beam, fluctuating bursts of fluorescence are observed with amplitudes related to the brightness of the molecular fluorescence and temporal properties that are related to molecular concentration and the diffusion coefficient. This is a very different method than single binding event detection of the nano-chem-FET. For example, nano-chem-FET has the advantage of not requiring the complex instrumentation necessary for confocal optical detection and is not affected by the photobleaching problems that occur in fluorescence fluctuation spectroscopy.

Fluctuation analysis of nanosensor data is optionally used to provide concentration of an analyte, e.g., given knowledge of the binding affinity and the number of binding sites per sensor, e.g., per nanowire. The concentration is also optionally obtained from the rate of new bindings if the bimolecular rate constant for binding and the number of sites is known. If binding characteristics are not available, however, the molecule is still detectable even though precise concentration information may not be.

Because different types of binding molecules affect the sensor signal differently, the specificity of a measurement is increased by discriminating analyte signal from background signal and distinguishing one analyte from another, permitting multiplexing. In particular, molecules differ with respect to the mean amplitude of the signal change, e.g., conductance of a nanowire, mean duration of a binding event, rate of new bindings. Ignoring effects due to diffusion limited transport to the sensor surface, the rate of new bindings is typically proportional to the product of the concentration and the bimolecular rate constant for binding. If the concentration is known, e.g., through other types of sensor date, then the rate constant for binding can be deduced. Changes in noise patterns are also optionally analyzed, e.g., because they are also subject to modulation by binding signals.

E. Nanosensor Arrays and Integrated Systems

The present invention utilizes nanostructures, e.g., as described above to provide substrates for chem-FET devices. The sensors can operate in the liquid or gas phase, opening up an enormous variety of applications, e.g., for integrated devices and for downstream applications. The detection schemes use inexpensive low voltage measurement schemes and detect binding events directly, so there is no need for costly, complicated and time-consuming labeling chemistries, e.g., fluorescent dyes, or the use of bulky and expensive optical detection systems. As a result, these sensors are inexpensive to manufacture and portable and are optionally used as implantable detection and monitoring devices. Finally, these nanomaterials can be assembled into massively parallel arrays at much higher densities than is achievable with current sensor array platforms and in a format compatible with currently available micro-fluidic systems.

The nanosensor arrays of the invention optionally comprise a plurality of functionalized nanostructures such as wires, a plurality of non-functionalized structures such as wires, or a combination thereof. In addition, arrays of functionalized nanowires optionally comprise the same functional group distributed throughout the array or a plurality of functional groups distributed to different portions of the array, e.g., for bacterial fingerprinting assays. In the discussions below and generally herein, nanowire embodiments are discussed for ease of description, but it will be appreciated that other nanostructures can also be used in the devices, methods and systems herein.

Each nanowire of the array is typically electrically connected, e.g., via two or more electrodes to a battery for applying a voltage across the nanowire and a detector, for detection of any changes in conductance of the nanowire. A single detector or a combination of detectors is optionally used to detect the signal from the array of nanowires. For example, each nanowire is optionally detected separately, such that a spatial array of individually functionalized nanowires can be used to quickly identify, e.g., a plurality of different pathogens bound to a bacteria. In addition, such arrays are typically used to detect patterns of components, e.g., from fragmented spores, or to detect cell migration as described below.

Because of the small size and ease of detection, the arrays of the invention are easily integrated into a variety of devices, e.g., a microwell plate or other sample container or a microfluidic device. The nanowires are optionally positioned in the devices after synthesis of the nanowire or positioned in the devices during fabrication. For example, positioning of free standing nanowires is typically done by flow based alignment of wires over chemically patterned surfaces that may or may not include electrical contacts. Where electrical contacts do not already exist on the substrate, electrodes are then patterned onto the field of immobilized, aligned wires to yield functional devices that include one or more wire connections.

Once arrays are constructed, they are typically contacted with samples, e.g., liquid solutions or gases, for analysis, e.g., to detect a particular component of interest in a sample solution. Sample solutions are typically presented to a nanowire array system, e.g., dropwise at a constant rate into a microwell, or microfluidic channel or reservoir, by flowing an uninterrupted or interrupted stream of sample into a channel, e.g., using pressure based or electrokinetic based flow. For more information on fluid flow in microfluidic systems, see, e.g., U.S. Pat. No. 5,779,868, to Parce et al., entitled "Electropipettor and Compensation Means for Electrophoretic Bias;" and U.S. Pat. No. 5,942,443 to Parce et al. entitled "High Throughput Screening Assay Systems in Microscale Fluidic Devices." Using either method of introduction, sample plugs, e.g., separated by buffer plugs, are produced that are optionally diluted into a stream of buffer, e.g., already present in the microchannel.

Example arrays include, but are not limited to the devices described below. In one embodiment, the present invention comprises a nanosensor array for detection of a change in charge. The array typically comprises a plurality of nanowires comprising one or more functional group that undergoes a change in charge when exposed to a component of interest. Typically, the functional group is an enzymatic substrate or a nucleic acid, e.g., a hairpin oligonucleotide. Glucose nanosensors are also provided. These sensors typically comprise one or more nanowires and glucose oxidase, wherein the glucose oxidase is proximal to the nanowires or immobilized on the nanowires. When the glucose oxidase comes into contact with glucose, the glucose is oxidized, resulting in a change in pH that is detectable via a change in conductance of the nanowire.

Figure 14:
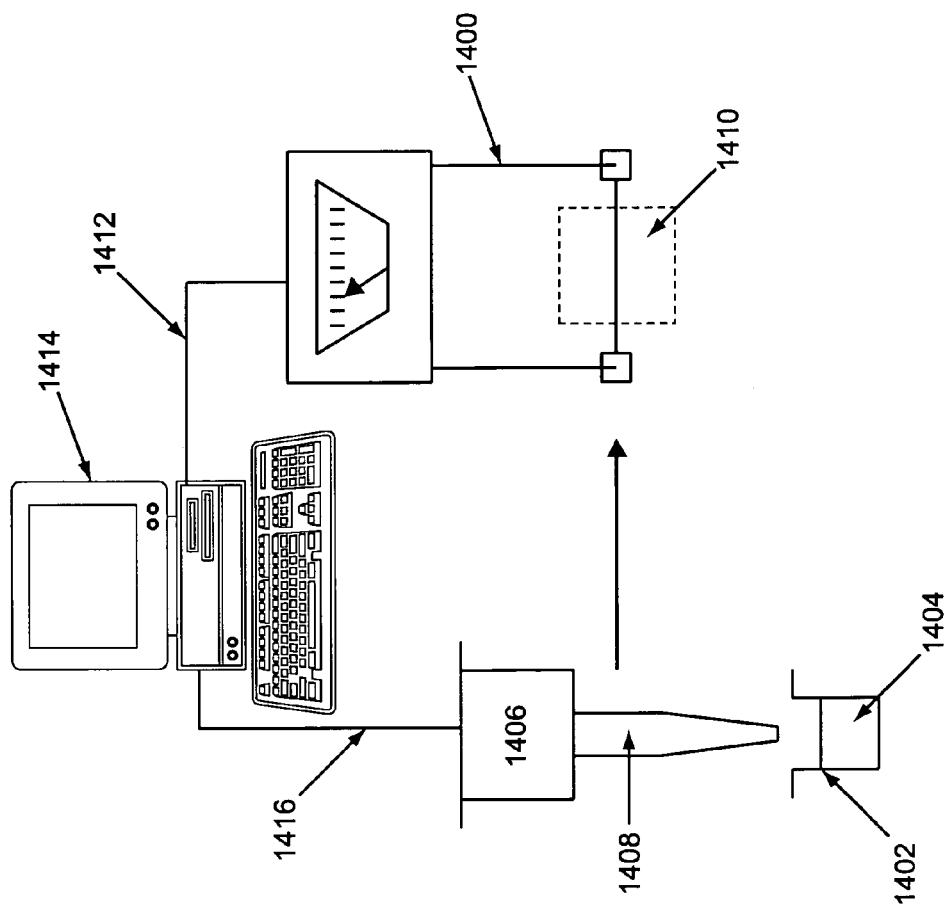
FIG. 14 schematically illustrates a system comprising a sensor in conjunction with a fluid handling system and processing and computing components to control operation of the sensor.

An example integrated sensor system is illustrated by FIG. 14. In addition to a nanowire sensor element or array of sensors, such systems typically include an electrical power supply, monitoring system for applying and measuring electrical current across the nanowire sensor element. For example, a simple ohm meter is optionally used to measuring conductance. Typically, high frequency ohm meters are used.

The systems of the invention also typically include data processing capabilities to enable the programmed operation of the sensors and to receive, store, and provide useful analysis and display of the data that is obtained. Typically, such processing capability is at least partially provided through an external computer 1414 that is coupled (via electrical cable or other operational connection 1412) to the power supply and monitoring portion of the system 1400. An operational connection can include one or more wires or cables, an infrared transmitter and receiver, a radio transmitter and receiver or any other connection typically used to transmit information between a central processor and a peripheral device or appliance. In addition to that portion of the processing capability provided by the computer, additional processor(s) may be integrated into the sensor system itself. By way of example, instruction sets that are routinely run during set up, operation and shut down are conveniently integrated into a sensor system. These typically include power adjustments, diagnostic operations, and the like. As used hereafter in the description, the processing capabilities of the overall system, whether internally or externally integrated with the overall system are referred to as the computer.

Typically, the computer includes appropriate programming to automate operation of sensor system 1400, as well as its ancillary components, e.g., fluid handling system 1406 via electrical cable/connection path 1416. This includes instructing the power supply in applying, regulating and/or modulating the current applied to the sensor, and instructing the fluid handling system, to the extent necessary, to deliver sample materials to the sensing surface of the sensor. The computer also will include programming that enables the receipt and storage of conductance data received from the sensor system 1400 in response to the application of sample material with the sensing surface. In addition, the computer will also typically be programmed to provide meaningful analysis of the conductance data. For example, the computer optionally includes programming that interprets conductance data received from the sensor and provides the user with a determination of the presence and optionally, the concentration of an analyte of interest. Such programming optionally includes access to a look-up table of known conductance values for different analyte concentrations. Alternatively, the programming compares conductance values against conductance values for a standard or control sample or range of control samples, and extrapolates or interpolates the concentration of the analyte of interest in the sample.

In addition to the basic elements, integrated systems of the invention also optionally include ancillary components to automate sample accession and delivery and provide data storage and analysis. For example, pipetting system 1406 in FIG. 14 is optionally used to deliver fluid samples, e.g., sample 1404, from sample vessels, e.g., vessel 1402, to reservoirs, e.g., reservoir 1410, to contact nanowire sensing surfaces which are coupled to reservoir 1410. Such pipettor systems are generally commercially available, e.g., from Beckman Instruments, Zymark Inc., and the like. Alternatively, or additionally, fluid handling systems are integrated into the sensor device using fluidic channel networks as described in more detail below. Examples are described in the literature, e.g., from Caliper Technologies Corp. For example, Fluidic elements are optionally incorporated into the sensor device by fabricating a channel or conduit containing layer over the insulator or semiconductor layer comprising the sensing element.

In a simple exemplary operation, and with reference to FIG. 14, a computer, at a user's initiation instructs fluid handling system 1406 to obtain a fluid sample 1404 from source 1402. In the case shown, this is accomplished by placing pipette tip 1408 into contact with fluid sample 1404 and drawing a portion of the fluid into the tip. The pipette tip is then translocated to a position over sensor reservoir 1410, at which point computer 1414 instructs the pipettor to expel the fluid into reservoir 1410. Although illustrated as a simple reservoir, sensing reservoir 1410 optionally includes a variety of fluidic components, including inlet ports and channel manifolds for delivering sample material to the sensing surface, or to multiple different or duplicate sensing surfaces. The computer then instructs sensor system 1400 to measure the response of the sensor to the sample material, and takes a measurement of that response and, based upon appropriate software, the computer analyzes the information and provides a user understandable display of the results of the analysis.

In some embodiments, the sensor elements or nanowires are incorporated into microwells. Typically, the wires are provided on substrates with ohmic contacts in place. The small chips are then positioned into microwells. The number of chips or devices in a microwell is variable. For example, to analyze a plurality of different samples for the same analyte, one sensor per well is typically sufficient. However, when multiplexing is desired, several sensors are optionally included in each well, e.g., each specific for a different analyte. When an array of microwells is constructed, each microwell optionally contains the same type of functionalized nanowire or a different type of functional group. In addition, each microwell is optionally used to test a different test compound, e.g., drug candidate, e.g., to provide high throughput screening.

In other embodiments, the sensors are incorporated into microfluidic systems. The microfluidic systems of the present invention are typically simple branched structures, but the exact configuration is variable and is optionally configured to adapt to a variety of different assays. Typically, multiple reagent wells connect to a central assay channel, wherein each well is optionally activated or deactivated by the application of pressure, e.g., positive or negative. By turning on one well at a time, plugs of reagents are created and flowed down the central channel, e.g., interspersed with plugs of buffer material. A series of reagents is typically tailored to perform all aspects of a given assay or assays. In some embodiments, multiple assays are optionally performed using the same array, e.g., a detection assay and a pH assay.

The reagent streams and sample streams typically intersect a buffer stream, e.g., to dilute the sample and/or reagent. In some embodiments, the two intersect such that the sample stream is on the bottom of the buffer stream. In this embodiment, the flow rates of the streams are such that the sample stream is a narrow stream placed below a wider stream of buffer. For example, the ratio of sample flow rate to buffer flow rate is typically on the order of 1:10. Typically, analytes diffuse across the boundary between sample and buffer, and the longer the streams are allowed to interact, the more material is transferred from the sample stream to the buffer stream. As a result, the concentration of analyte at the bottom of the sample stream decreases as a function of distance traveled along the channel after the mixing point. In the case of bacterial cells, viruses, and spores, there is typically little diffusion, so a roughened top surface of the mixing channel is optionally used to mix the two layers actively, e.g., again resulting in more complete mixing as the sample proceeds farther along the channel.

Microchannels comprising nanowire arrays typically comprise nanowires positioned at one or multiple locations or positions along the channel. These areas are referred to herein as array capture fields or detection regions. An "assay capture field," "capture field" or "capture region" is typically a region or section of a device, e.g., a microchannel or other substrate, that contains a functional group that binds to or captures a component of interest, e.g., by specifically binding the component. In the present devices, the capture regions are typically sections of microchannels that have nanowires, e.g., functionalized nanowires, disposed therein. For example, a plurality of phage functionalized nanowires is optionally used as a capture region in a microfluidic channel. Alternatively, non-functionalized nanowires are used to non-specifically capture cells in a microchannel. A particular channel or substrate is optionally constructed to contain multiple capture regions for capture of different components or to capture different concentrations of a component of interest as described above.

Figure 11B:
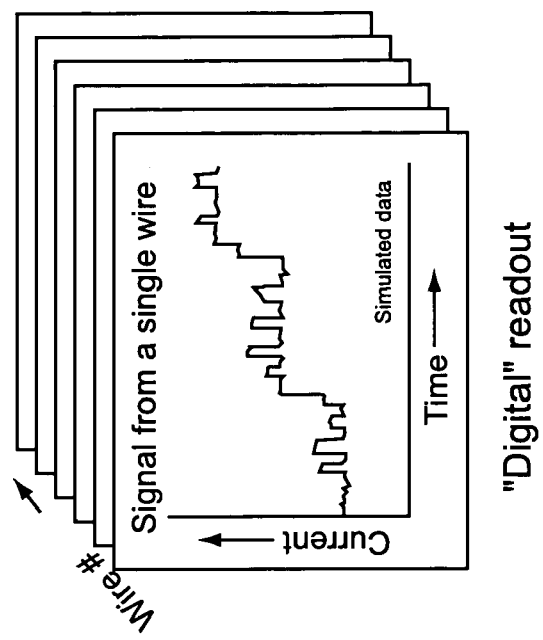
FIG. 11B provides simulated data for an assay of FIG. 11A.
Figure 11A:
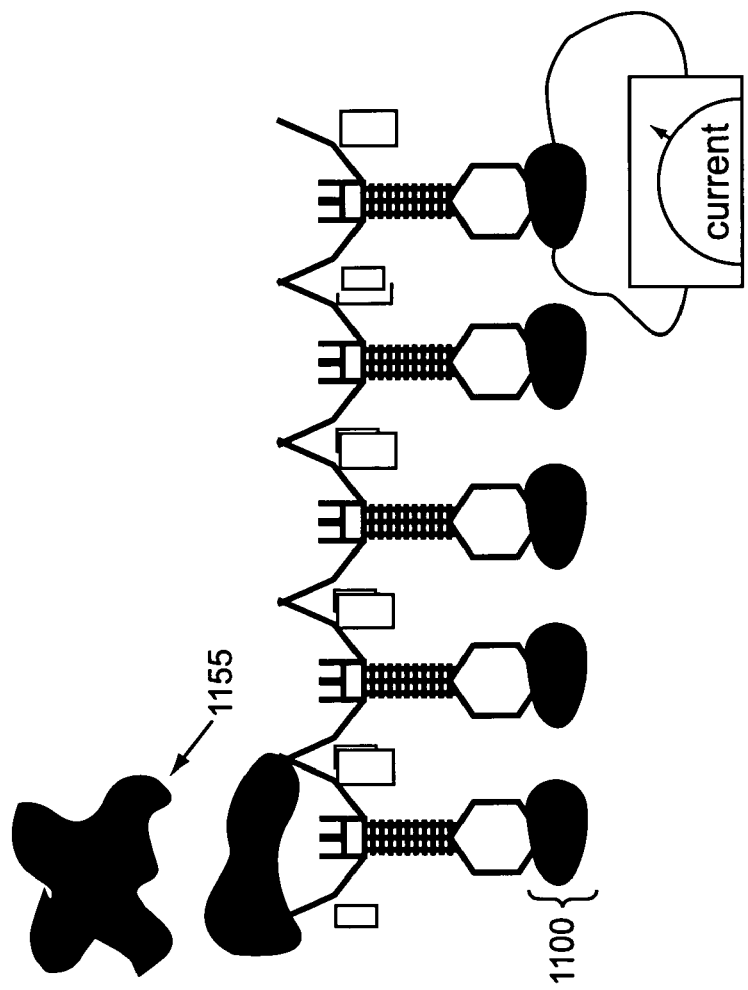
FIG. 11A is a schematic illustrating detection of a component of interest on a nanowire.

The capture of varying concentrations of a component of interest provides a large dynamic range in an assay where the signal is typically digital. A digital signal is typically used because cells are typically about 1 micron in size, which is comparable to the length of a single wire. For example, rod like vegetative cells are typically about 0.5 to about 2.5 µm wide and about 1.2 to about 10 µm long and spores are typically about 1 to about 2 µm in diameter. See, e.g., Dixon et al., (1999) NEJM 341:815. As a result, the number of binding events per nanowire is typically low and each event results in a quantized change in conductance of the nanowire. By changing the concentration of the analyte over the length of the channel, the overall dynamic range is extended as the assays, are repeated periodically over the length of the channel. By selecting the mixing rate and the spacing between assays, e.g., spacing between nanowires, the dynamic range is optionally increased or decreased. An example of a digital readout is provided, e.g., in FIGS. 11A and 11B. FIG. 11A illustrates binding of cells 1155 to nanowire array 1100. A digital signal is obtained for each nanowire in the array as pictured in FIG. 11B, wherein each stepwise change indicates a binding or release event and the assay signal.

In fact, the dynamic range in the above devices is optionally controlled at two levels. First, the binding event is controlled by a change in concentration as a function of position along the length of the assay channel or detection region. In this situation, a capture field closest to the input end of the channel experiences the highest concentration of analyte in the sample. If this concentration is so high that the signal is saturated, then the next capture field, which experiences a lower concentration of analyte, is optionally used, e.g., because the lower concentration brings the signal into the linear regime of the assay. Additional assay capture fields are optionally used such that at some point along the channel, the concentration is low enough to allow quantification of the signal. On the other hand, if the concentration of the analyte in the sample is low, the first capture field experiences the highest concentration, giving that position the highest sensitivity. By monitoring the number of binding events per location in channel, the system can automatically choose the appropriate region of the assay channel to collect data.

The second level at which the dynamic range is optionally controlled is in detection via change in pH or change in charge. Depending on the rate of proton production by the cells, e.g., in the capture region, either a high or low sensitivity detector is preferred. Accordingly, the potential on each wire is optionally modified to bring the sensitivity within the dynamic range of the particular wire.

In addition to running consecutive assays, e.g., with multiple concentrations to increase dynamic range, the devices of the invention are also typically constructed to comprise multiple sets of functionalized nanowires arrayed along the channel. For example, a series of multiplexed fields is optionally created by positioning capture fields with phage and/or antibodies specific to different organisms along the channel. The different fields are then arrayed along the channel to provide detection at different concentrations as well. Preferably, the spacing between fields is large enough such that there is no significant diffusion of protons between the field to disrupt accurate pH measurements in each field. For example, typical spacing between fields is about 0.1 µm to about 10 mm, between about 0.5 µm and about 5 mm, or between about 1.0 µm and 1.0 mm. Channel width and field length are typically selected to optimize the number of binding events per field.

The devices of the invention are typically reusable. For example, after an assay has been performed, the device is optionally cleaned, and/or washed such that it can be reused. Washing an assay capture region is typically accomplished by flushing the system, e.g., the channels, with a denaturing solution such as concentrated urea, guanidinium chloride, a high or low pH solution. The result of the flush is that the binding moieties on the nanowires release their analyte and the capture field is refreshed and available for another measurement. When washed, the signals in the nanowires, e.g., the functionalized and non-functionalized or the binding detector and the pH detector, typically revert to a steady state condition or signal.

FIG. 8, Panels A and B, illustrates an example configuration for a nanosensor integrated into a microfluidic system. The system comprises detection region 805 comprising one or more nanowire arrays. Reagents and samples are flowed into the detection region, e.g., through buffer input channel 810, or sample input channel 815. Typically, buffer channel 810 delivers fluid into the top portion of detection region 805 and sample channel 815 delivers fluid into the bottom portion of detection region 805. Alternatively, only one input channel is used. Various reservoirs are optionally used to deliver sample materials, reagents, buffers, and the like into input channels 810 and 815. For example, reservoirs 820, 825, and 830 are optionally used to deliver reagents, e.g., a glucose solution, into detection region 805. Reservoir 840 is optionally used to deliver sample into input channel 815 and various buffer reservoirs are typically provided for dilution of the reagents, e.g., prior to delivery into the detection channel, or for separating a sample solution into discrete sample plugs. For example, a sample and buffer are flowed from reservoirs 840 and 850 to form sample plugs, e.g., sample plugs 842, 844, and 846, and buffer regions, e.g., regions 852 and 854. When a sample plug from input channel 815 meets a corresponding sample plug from input channel 810, the sample plug is not diluted into a buffer stream as it flows through the detection region. However, a if the sample plug intersects with a buffer region flowing in from input channel 810, the sample is diluted into the buffer to produce a concentration gradient in detection region 805 as described above. Alternatively, the same solution is flowed through inputs 810 and 815 to provide a homogeneous solution instead of a concentration gradient. Various reagent and/or sample wells are also fluidly coupled to buffer input channel 810, e.g., reservoirs 860, 865, and 870. These reservoirs typically contain the same reagents as reservoirs 820, 825, and 830, e.g., to provide intersecting regions that are not diluted by the buffer stream.

FIG. 8B provides a schematic illustration of detection region 805. Detection region 805 typically comprises one or more array capture fields, e.g., capture fields 875 and 880. Typically, an array capture field comprises one or more functionalized nanowires comprising one or more binding moiety linked thereto. The functionalized nanowires are optionally the same in each capture field or different. Alternatively, one capture field optionally comprises multiple functional groups. For example, as illustrated, each capture field 875 and 880 comprises one or more nanowires comprising binding moieties that bind to e. Coli, plaque, and anthrax, e.g., binding moieties 885, providing 3 subfields. Therefore, a sample flowed through the detection region 805 is monitored for each of these organisms. The binding moiety is optionally selected to bind a whole organism or cell, e.g., a live cell, or to bind to one or more components of an organism, e.g., for organisms that have been fragmented prior to detection. In addition, the multiple capture fields are typically used to detect a component of interest, e.g., a cell, at multiple concentrations, e.g., providing two or more positions along the channel at which the organisms are optionally detected. When a concentration gradient is applied to the sample stream in the channel, the two capture fields are exposed to different concentrations of samples and are used to detect the sample at both concentrations, e.g., as described above.

In an alternative configuration, devices of the invention comprises non-functionalized nanowires positioned proximal to functional groups linked, e.g., to a channel surface. For example, the binding moieties or functional groups, e.g., capture antibodies or phages, are optionally affixed to the channel surface with nanowires positioned proximal thereto. A captured cell or other organism induces a change in the signal from the nanowire or the pH alone is optionally used to determine the presence of the cells of interest. Alternatively, nanophysiometry is optionally used to determine presence and viability, e.g., using the basic pH assay to determine viability and a secondary labeling or ELISA type assay to determine presence of cells. One advantage of this system is that it is inherently reversible. Therefore, there is no need to remove analytes that were bound to the nanowires prior to reuse of the device. Capture moieties can be affixed to the surface of the channel in vast excess of the analyte, e.g., such that binding density is limited by steric factors. Therefore, when the device is denatured to prepare a next use, if any binding ligands are destroyed in the process it would have little effect on the quantification of the next assay.

Any of the above devices, components, arrays or systems described above is optionally used, e.g., in any configuration, to perform the assays described below.

II. Detection of a Component of Interest

In one aspect, the present invention provides nanosensors, e.g., for detection of a component of interest. The nanosensors of the inventions typically comprise one or more nanowires, e.g., an array of nanowires in a microfluidic device as described above. The nanowires are optionally functionalized or non-functionalized nanowires and are typically tailored to detection of a specific component of interest. The methods by which a component of interest is optionally detected vary as described in more detail below. For example, in one embodiment, nanowires functionalized with a binding moiety are used to detect a component of interest that specifically binds to the binding moiety. The binding alters the conductance of the nanowires, which alteration produces a detectable change, e.g., a change in current or voltage.

A "component of interest" as used herein refers to any analyte for which detection and/or analysis is desired. Typical components of interest include, but are not limited to, proteins, polypeptides, peptides, amino acids, nucleic acids, oligonucleotides, nucleotides, enzymes, enzyme substrates, carbohydrates, lipids, other organic compounds, sugars, alcohols, polymers, cells, spores, toxins, drugs, bacteria, antibodies, phage, and the like.

In addition to detection of a binding event, the nanosensors of the present invention also provide detection based on a change in charge, e.g., on or near the nanowire, a change in pH, a fragmentation pattern, and the like. Furthermore, the nanosensors of the present invention are useful in detecting multiple concentrations or cellular responses at multiple concentrations of test compound. Each of these techniques is described in more detail below.

A. Detection of a Component of Interest via a Change in Charge

In addition to sensing a binding event, a nanowire is optionally used to detect a charge change event, e.g., a change in charge or a charge redistribution. Typically, a change in a charge to a molecule that is proximal to or linked to a nanowire results in a change in the conductance of the nanowire. Because nanowires are optionally functionalized, e.g., as described above, with biological molecules such as proteins, peptides, oligonucleotides, and the like, the nanowires are optionally used to sense or detect when a biological molecule has been modified, e.g., by a change in charge.

In one embodiment, one or more nanowires comprising a functional group or binding moiety is optionally contacted with, e.g., exposed to, a solution comprising a component of interest. For example, a solution is optionally flowed over a nanowire array in a microchannel or deposited onto a nanowire array in a microwell such that the component of interest can interact with the array. The component of interest reacts with, binds to, or otherwise interacts with the functional group to produce a change in charge on the functional group, e.g., a change in the value of the charge associated with the functional group or a redistribution of charge. The change in charge alters the conductance of the nanowire and thereby provides a detectable signal.

For example, to monitor enzymatic activity by detection of a change in charge, the functional group linked to a nanowire is one that undergoes a change in charge, e.g., in the value or distribution of the charge, e.g., upon exposure to some catalyst or analyte of interest. A "change in charge" refers herein to a change in the value of a charged molecule, e.g., a change from a positive charge to a negative charge, a change from zero charge to a positive charge, a change from a charge of −1 to −3, or the like, or a change in charge distribution, such that the conductance of the nanowire is altered. For example a change in charge from a redistribution occurs when a highly charged molecule is moved away from a nanowire, e.g., by an interaction with a component of interest.

Enzyme activity is optionally assayed in this manner. For example, enzymatic modification of a biological molecule is optionally detected using a nanowire that is functionalized with an enzymatic substrate. Upon exposure to or contact by the enzyme, the substrate undergoes a change in charge or a charge redistribution. Many enzymatic modifications result in a change in charge. For example, kinases catalyze the addition of a phosphate group to a protein or peptide resulting in a net gain of 2 negative charges. A phosphatase does the reverse, e.g., moving a phosphate group for a net loss of 2 negative charges. A protease cleaves a protein or peptide substrate and if charged residues are removed by the cleavage, the cleavage is optionally detected by a nanowire functionalized with a protease substrate. DNA polymerases, ligases, transferases and the like add nucleotides or nucleic acid subsequences to an extending nucleic acid chain, thus increasing the total negative charge on the oligonucleotide. Any enzyme that modifies the substrate such that the product has a different charge is optionally analyzed by the methods of this invention.

"Enzyme" is used herein to refer to any biological catalyst. For example, biological catalysts are typically molecules, e.g., proteins, nucleic acids, or the like, that catalyze cellular reactions. Enzymes used in the present invention are optionally proteins, DNA, RNA, or the like. The enzymes of the invention are optionally naturally occurring enzymes, or non-naturally occurring enzymes, e.g., recombinant or mutated enzymes. In addition, the enzymes are optionally isolated and/or purified prior to use in an assay. "Enzymatic activity" is used herein to refer to the action of the enzyme in catalyzing a reaction, e.g., the modification of a substrate. Enzyme activity is optionally detected using the methods of the present invention as described below.

An "enzyme substrate" is any molecule which undergoes a reaction catalyzed by an enzyme. Typically the enzymatic substrate binds to the enzyme and undergoes a change or modification catalyzed by the enzyme, to yield one or more products. For example, proteases typically degrade their substrate, e.g., proteins or peptides, into amino acids and/or smaller peptides. Typically, an enzyme binds to the substrate to facilitate a modification of the substrate, e.g., addition or removal of a phosphate group, or cleavage of the substrate molecule. Typical substrates include, but are not limited to, proteins, nucleic acids, peptides, oligonucleotides, and the like.

"Nucleic acid" "oligonucleotide", and "polynucleotide" are used interchangeably herein to refer to polymers of nucleotides, e.g., ribonucleotides or deoxyribonucleotides (including analogues thereof, including peptide nucleic acids, locked nucleic acids, or the like), typically, though not always (e.g., in the case of PNAs) linked through a phosphodiester bond. The nucleic acids of the invention optionally include any naturally occurring nucleotides and/or natural or artificial nucleotide analogs and or mimetics thereof, optionally including alternative base or backbone structures known to those of skill in the art.

The terms "polypeptide," "peptide," and "protein" are used interchangeably herein to refer to a polymer of amino acids, typically linked through peptide bonds. Polypeptides of the invention include, but are not limited to, proteins, biotinylated proteins, isolated proteins, recombinant proteins, enzymes, enzyme substrates, and the like. In addition, the polypeptides or proteins of the invention optionally include naturally occurring amino acids as well as amino acid analogs and/or mimetics of naturally occurring amino acids, e.g., that function in a manner similar to naturally occurring amino acids.

Figure 2:
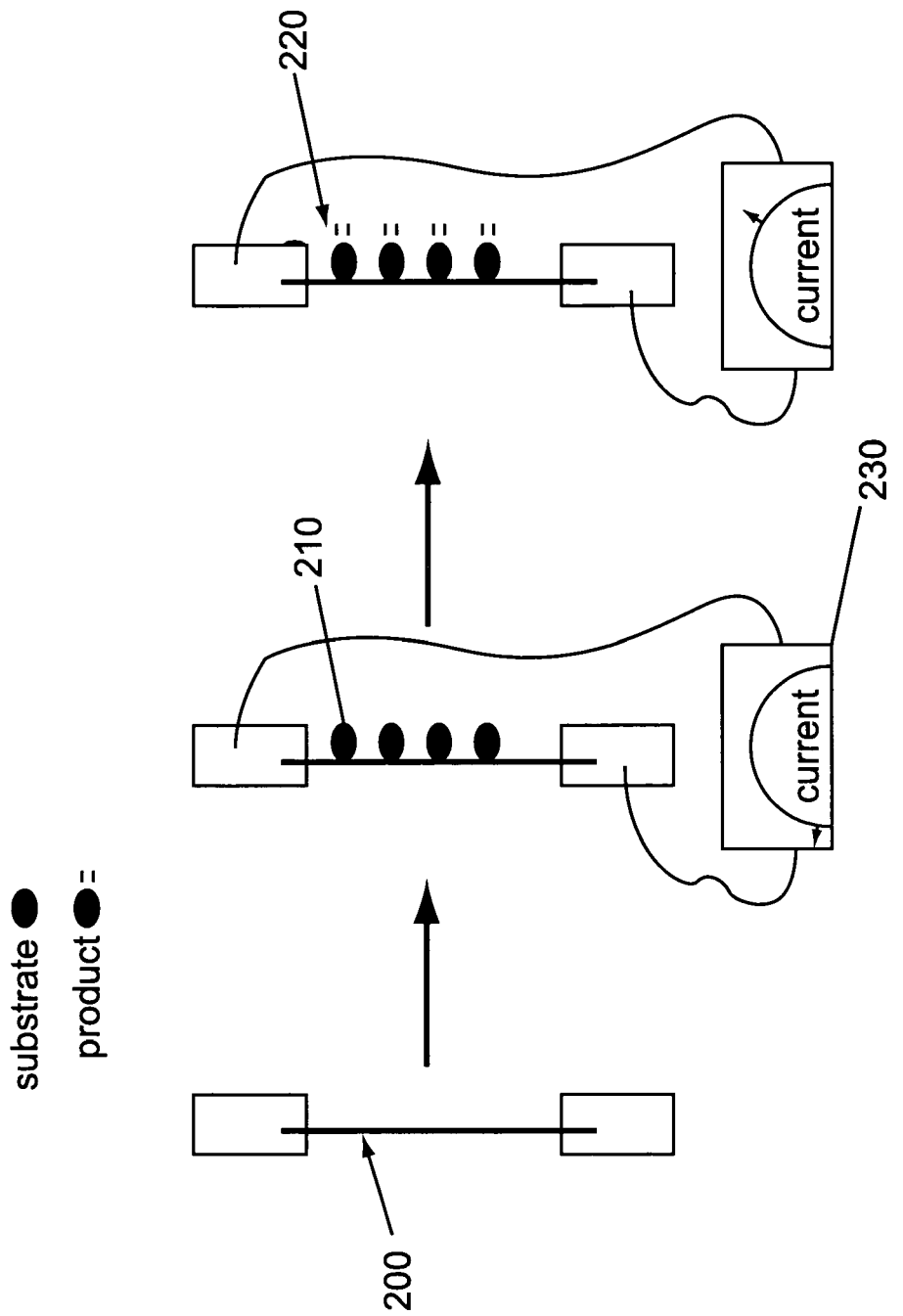
FIG. 2 is a schematic illustration of a nanosensor used to detect enzymatic activity by detection of a change in charge of the substrate

A schematic representation of a nanosensor for use in detecting enzymatic activity is provided in FIG. 2. FIG. 2 shows nanowire 200, which is functionalized with enzymatic substrate 210. The enzyme that acts on the substrate functional group is mixed with the nanowire to produce a product, e.g., modified substrate 220. The modification of the substrate produces a change in charge that is detected, e.g., as a change in conductance and measured by detector 230. In the example shown, the product of the enzymatic reaction has a net increase of two negative charges compared to the enzyme substrate. The change is detected as a change in conductance of the nanowire.

In another embodiment, the change in charge comprises a redistribution of charge. For example, a functional group comprises a charged moiety linked to or positioned proximal to a nanowire. Upon a change in conformation of the functional group, the charge is redistributed relative to the nanowire. For example, binding of a component of interest to a functional group that causes a change in conformation of the functional group can move the charge moiety away from the nanowire, thereby changing the conductance of the nanowire.

For example, the functional group is optionally a nucleic acid such as a hairpin oligonucleotide. Hairpin oligonucleotides of the present invention typically, comprise a first end, a second end, and a central portion. The first end and the second end are complementary to each other, e.g., the nucleotides in the first end form base pairs with the nucleotides in the second end. The central portion is typically complementary to and binds to the component of interest. Typically, either the first end or the second end is linked to the nanowire and the other end comprises a charge moiety. The first end also typically comprises a charge moiety that is proximal to the nanowires, e.g., a latex bead (about 50 nm in diameter) comprising a carboxylate or amine surface, a nucleic acid, a highly charged polypeptide, a charged polymer, one or more negatively charged nucleotides, a metal nanocrystal, or the like.

When the oligonucleotide is folded into a hairpin, e.g., hydrogen bonds are formed between the first end and the second end, the charge moiety is positioned proximal to the nanowire. When the oligonucleotide unfolds, e.g., the hydrogen bonds linking the first end to the second end are disrupted, the charge moiety is moved from proximity to the nanowire. The oligonucleotide is optionally used to detect a component of interest, e.g., a polymorphic allele or a portion of a gene sequence of interest, by selecting a central portion of the hairpin oligonucleotide that binds to the component of interest, such that when a solution comprising the component of interest is present, the hairpin unfolds and moves the charge moiety away form the nanowire. The removal of the charge moiety changes the charge distribution in the vicinity of the nanowire and produces a change in conductance, which is detected, e.g., electrically or digitally. When the nanowire is contacted with a solution comprising the component of interest, the component of interest binds to the central portion of the hairpin oligonucleotide and the hairpin unfolds or linearizes, e.g., the hydrogen bonds between the first end and the second end are broken. The unfolding moves the charge moiety away from the nanowire, thereby redistributing the charge of the functional group. The redistribution of charge produces a change in signal from the change in conductance of the nanowire. The signal is detected, thereby providing detection of the component of interest, e.g., an oligonucleotide that is complementary to the central portion of the hairpin. The hairpin provides a specific system that releases the highly charged molecule from the surface only when the component of interest specifically binds to the central portion of the hairpin. For more information on hairpins that unfold upon binding of a component of interest to a central portion, see, e.g., U.S. Pat. Nos. 5,118,801, 5,312,728, 5,439,793, 5,925,517, 6,103,476, 6,277,607, and 6,365,729 directed, e.g., to molecular beacons and hairpin primers.

The redistribution of charge is also optionally used to amplify a signal in a chem-FET. Typically, chem-FETs do not provide enough sensitivity, e.g., for detection of nucleic acid hybridization. The low sensitivity of chem-FET is overcome by introducing and/or removing a highly charged moiety to the FET surface that only occurs during a specific binding event. This approach provides a chem-FET with increased sensitivity and is optionally used with nano-chem-FET to change the dimension requirements to allow for thicker wires, e.g., that are optionally made with conventional lithography techniques. For example, the component of interest binds to the hairpin, causing it to unfold and moves a charge moiety away from the nanowire, thereby increasing the signal produced by binding of the oligonucleotide to the hairpin oligonucleotide.

Figure 5:
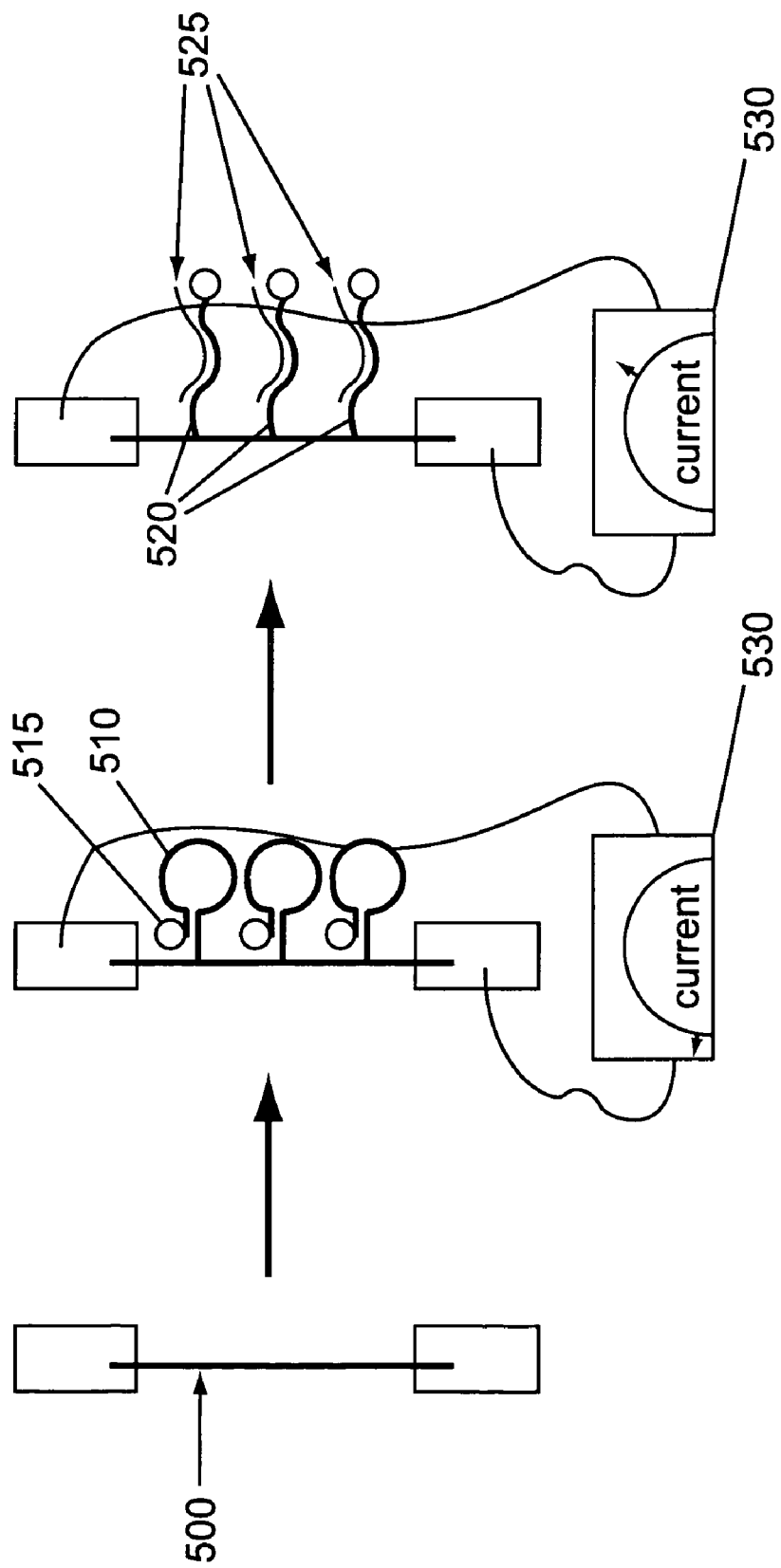
FIG. 5 illustrates introduction of a highly charged molecule to the surface of a FET using a hairpin oligonucleotide.
Figure 6:
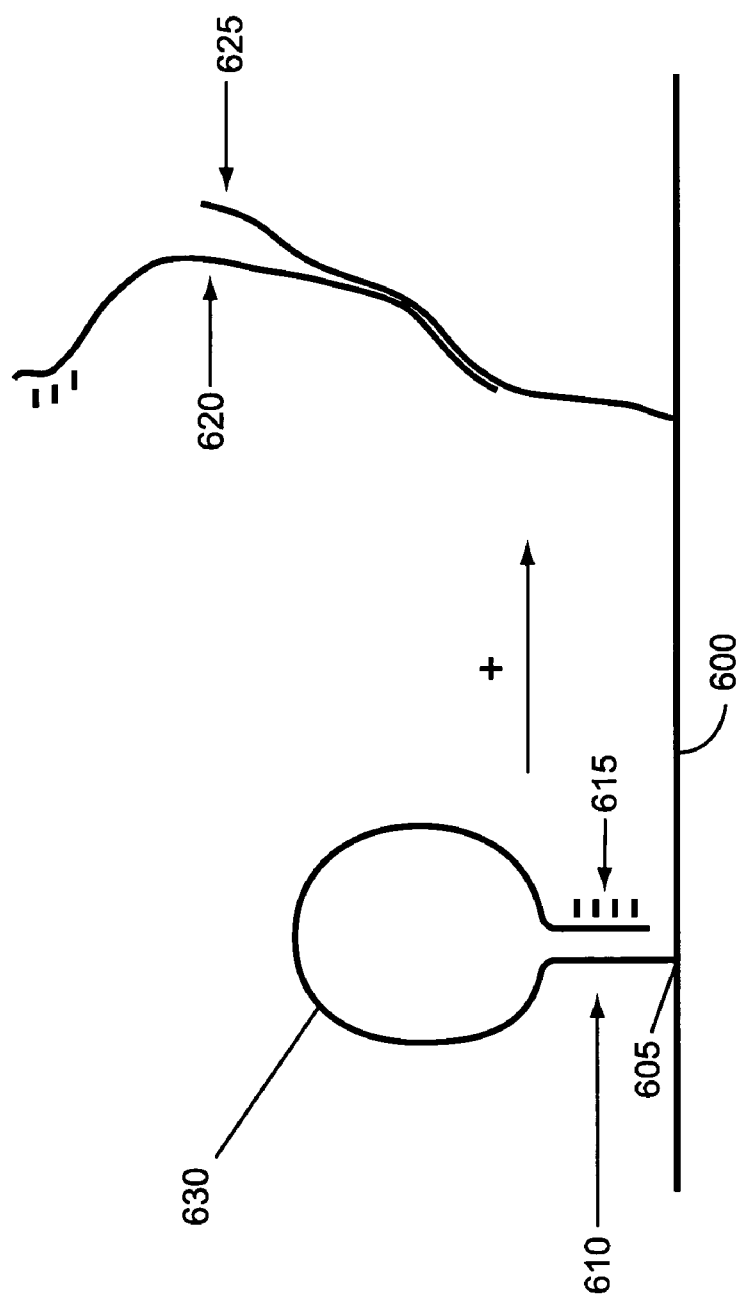
FIG. 6 illustrates an alternate use of the hairpin oligonucleotide in which the hairpin itself comprises the highly charge moiety.

FIG. 5 illustrates the use of a charge moiety at the surface of a FET is used to detect a component of interest or amplify a signal from a component of interest. FET substrate 500 is functionalized with hairpin 510 comprising charge moiety 515. A sample comprising a component of interest is added to the FET surface. The component of interest binds, e.g., specifically, to a portion of hairpin 510, resulting in linearized hairpin 520 bound to component of interest 525. The change in conductance of substrate 500 upon the removal of charge moiety 515 is detected by detector 530. An alternate version of the hairpin/charge moiety combination is provided in FIG. 6, wherein the charge moiety comprises one or more negatively charged nucleotides on one end of the hairpin, e.g., the end that is not physically linked to the FET substrate. For example, hairpin 610, wherein first end 605 is attached to nanowire 600 and second end 615 comprises about 1 to about 6 negative nucleotides, which nucleotides form the charge moiety of the hairpin. Target molecule 625 binds to central portion 630 of hairpin 610, causing the hairpin to unfold into unfolded hairpin 620, in which negative nucleotides on second end 615 are removed from the surface of nanowire 600.

Nanosensors for the detection of enzymatic activity as described above are another embodiment of this invention. The nanosensors typically comprises a nanostructure element comprising a functional group that is capable of changing charge or redistributing charge in the presence of an analyte of interest, so as to yield a detectable change in the nanostructure. The nanostructure is typically a nanowire, but is also optionally a nanotube, nanorod, or the like. In addition, an array of nanowires is also optionally used. The entire array is optionally used to detect a single component, or the array optionally comprises different functional groups that are analyzed simultaneously, e.g., to detect activity for a plurality of enzymes in a multiplexed assay. For example, an array optionally comprises a plurality of nanowires with a plurality of different functional groups, each capable of changing or redistributing charge in response to a different analyte. The nature of the linkage between the functional group and the nanostructure is variable. Any method of functionalizing is optionally used that positions the functional group such that is able to interact with, e.g., bind to, and be modified by the component of interest. Functional groups are likewise variable as described above. Typical functional groups for nanosensors of this type include, but are not limited to, enzyme substrates such as proteins and hairpin oligonucleotides as described above.

In addition to devices and methods for detecting change in charge, the present sensors are also used for detection of other events, e.g., pH changes, as described below.

B. Detection of a Component via Detection of a Change in pH

In addition to detection of a change in charge, the nanosensors of the invention are optionally used to detect a change in pH. This is especially useful in the detection of reactions or components that produce a change in $H^+$ concentration. In particular, the present invention provides a glucose sensor and methods of detecting glucose by a change in pH.

Typically, the methods comprise providing one or more nanowires comprising glucose oxidase immobilized thereto or proximal thereto. The enzyme can be but does not have to be attached to or immobilized on the nanowire; it can also optionally be placed in the vicinity of or proximal to the nanowire. Because the nanowire detects a pH change, i.e., a change in $H^+$ concentration, the nanowire does not need to be attached to the enzyme, it can simply be positioned such that any changes in the solution will be experienced by the nanowire. For example, the enzyme is optionally placed in a microwell with one or more nanowires. The nanowires are then contacted with a test solution, e.g., one containing glucose. Any glucose present in the test solution is oxidized by the glucose oxidase resulting in a change in pH of the test solution. The change in pH produces a signal in the nanowires, which is detected, thereby detecting the glucose in the test solution.

The reaction resulting in the increase in $H^+$ concentration is typically between glucose and oxygen, which combine in the presence of glucose oxidase to produce a mixture of gluconic acid and hydrogen peroxide, thereby producing a change in local pH. The change in pH is proportional to glucose concentration; therefore, a nanowire in the vicinity of the reaction detects the change in pH and is optionally used to thereby detect the presence of and/or concentration of glucose in the sample.

In another embodiment, the present invention provides glucose sensors, e.g., more sensitive glucose sensors than presently available. A glucose sensor of the invention typically comprises a nanowire or array of nanowires comprising glucose oxidase either immobilized thereto, e.g., bound to the nanowire as described above, or proximal to the nanowire, e.g., located in the vicinity such that the glucose oxidase can catalyze a reaction between glucose and oxygen. For example, a microfluidic channel or other substrate is optionally derivatized with glucose oxidase and an array of nanowires positioned proximal to the glucose oxidase such that they detect any changes in pH due to reactions involving the enzyme.

Although the example presented herein is a glucose sensor, other sensors are also optionally constructed for any reaction that results in a change in pH. For example, a non-functionalized wire or amine-modified nanowire is optionally used to detect a change in pH due to cellular metabolism, e.g., glucose metabolism, or any other metabolic process that changes the local pH. For more information on detection of cellular metabolism, see, e.g., *Biosensors and Bioelectronics* 7:255-272, (1992), by Owicki and Parce.

In a similar manner, a redox potential is optionally measured. In a potentiometric electrochemical system, a dominant redox couple is typically present, e.g., ferricyanide/ferrocyanide, that sets the surface potential of an electrode, e.g., in a way that is comparable to a pH-electrode system in a buffer. A redox potential is proportional to the log of the ratio of the oxidized to reduced species. A nanowire for detecting a redox potential is typically coated with a metal, e.g., a silicon nanowire coated with a thin layer of metal, e.g., zinc. A system that involves an enzyme that catalyzes a redox reaction is optionally coupled to a ferricyanide/ferrocyanide system and detected in a similar manner to what is described above.

C. Use of Pyrolysis to Detect Cellular Components

In another embodiment, the present invention provides methods of detecting cellular components or fragments. The methods typically involve heating one or more cells or spores to provide cellular fragments. The cellular fragments are typically deposited on one or more nanowires and detected. For example, an anthrax spore is optionally detected by identifying a pattern of fragments, using a nanowire array functionalized with various binding moieties that bind specific components found, e.g., in an anthrax spore.

A "cell" or "biological agent" as used herein optionally includes any of: a bacterial cell, a plant cell, a fungal cell, an animal cell, a spore, a viral particle, a protozoa, plasmodium, and/or the like. In addition, the cells are optionally of any type known to those of skill in the art, e.g., muscle cells, blood cells, germ cells, epithelia and/or the like. For example, the cell is optionally a mammalian blood cell or tissue cell (e.g., from primary or secondary culture), or a spore such as an anthrax or other pathogen spore, or the like. Cells are optionally fragmented to provide, e.g., sections of membranes, mitochondria, nuclei, lysosomes, peroxisomes, golgi, cyrtoplasm, various proteins, e.g., cytosolic and membrane, and/or the like, and in the case of plants, chloroplasts are optionally obtained.

The methods typically comprise the use of pyrolysis to breakdown the cells so that fragments within the cell are directly detectable, e.g., on a functionalized nanowire. The methods provide detection of cellular components by first heating the biological agent to break it into two or more fragments. In some embodiments, agents to aid fragmentation of the cell, e.g., cell disruption agents, are optionally added to the cells during the fragmentation process, e.g., to aid in the destruction of the plasma membrane or cell wall. For example, a surfactant or detergent is optionally added to the cells thereby lowering the temperature necessary for fragmentation. After fragmentation by pyrolysis, the fragments are typically analyzed using a functionalized nanowire, e.g., comprising one or more functional groups that specifically bind to or otherwise interact with one or more cellular fragments, e.g., a target molecule or fragment within the cell.

In some embodiments, the cells are fragmented and then processed prior to detection. For example, the fragments are optionally filtered, e.g., by condensing gaseous phase fragments by flowing the gas phase over a cold surface and then filtering the fragments on a column. In other embodiments, processing includes separation, e.g., using an electrical field to accelerate charged fragments to separate roughly by mass and/or charge. Processing refers to any step that is taken to prepare the fragments for detection, e.g., to aid in the detection process. For example, samples are optionally filtered, condensed, separated, or heated prior to detection.

Detection of the cellular fragments typically comprises binding the components to one or more functionalized nanowires. For example, a pattern of cellular fragments is optionally used to rapidly identify a particular combination of components, e.g., components associated with a particular disease, e.g., cancer, or components associated with anthrax, AIDS, or the like. A pattern of fragments refers to a particular combination of elements detected, e.g., a certain percentage of a first component, e.g., compared to a certain percentage of a second component or to a pattern associated with a particular combination bound to an array of nanowires.

For example, a spatial array of functionalized nanowires is optionally constructed e.g., in a microchannel, for binding a plurality of cellular fragments. Each portion of the array optionally comprises a different functional group, e.g., that binds a different cellular component. When the cellular fragments bind to the array, a binding pattern on the array is easily identified and compared, e.g., to standards having known or predetermined binding patterns.

Figure 4:
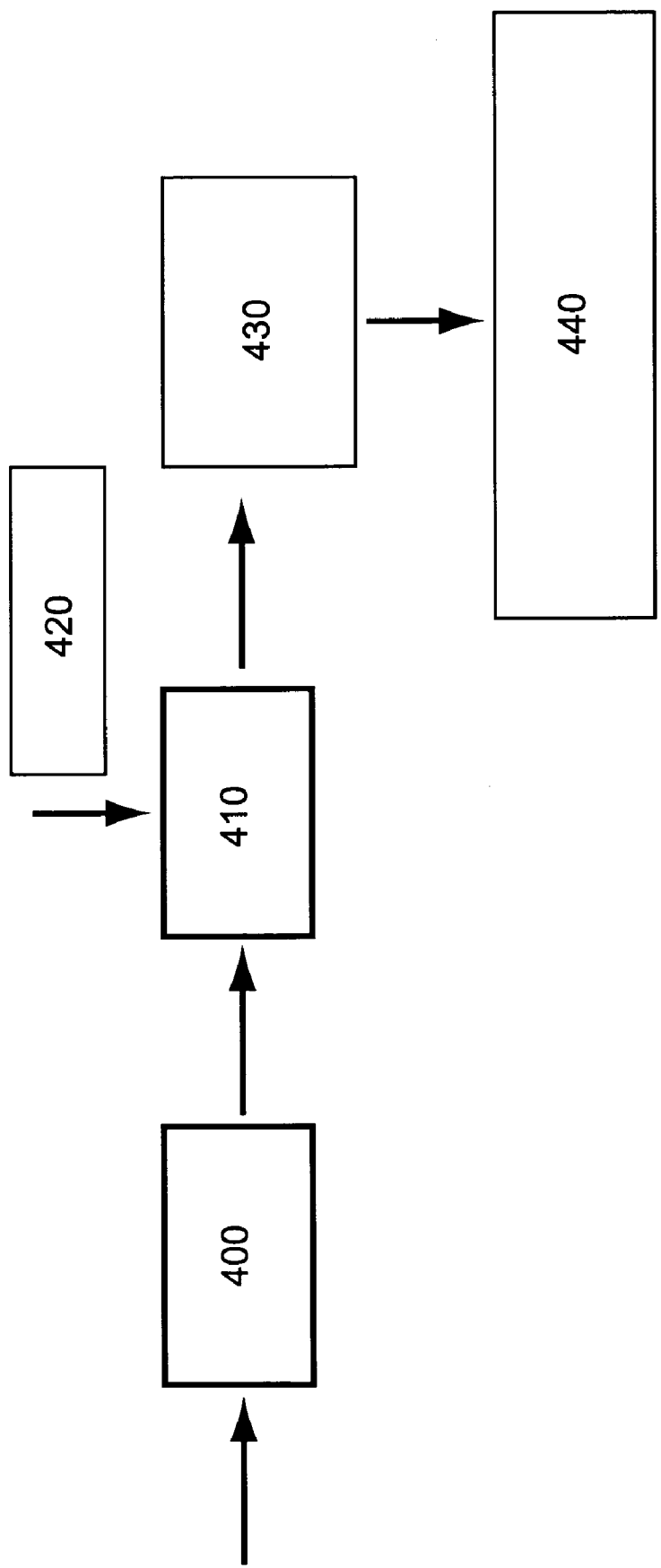
FIG. 4 is a schematic illustration of a device for cell analysis.

Devices for rapid detection of cellular fragments or biological constituents are also provided herein. The devices typically comprise a pyrolysis chamber for heating a biological agent of question, e.g., a cell or spore, and a nanowire or nanowire array for detection of the fragments. An example apparatus is illustrated in the schematic of FIG. 4, in which pyrolysis chamber 410 is coupled to air intake 400. A "pyrolysis chamber," as used herein, is typically an enclosed chamber for heating one or more cells or other materials. The chamber typically comprises an air intake for the introduction of air into the chamber and is heated, e.g., using any heating element known to those in the art, such as a resistive heater, a Peltier heater or the like. The materials in the chamber are typically heated to form a gas phase comprising the fragmented materials.

Typically air, e.g., a fixed volume, is drawn into the pyrolysis chamber, e.g., to which a biological agent has been added, and heated to fragment the biological agent. In some embodiments, agents to aid fragmentation are optionally added to the pyrolysis chamber, e.g., agent 420. For example, a surfactant is optionally added to disrupt the cell wall and lower the temperature required for pyrolysis. Once fragmentation occurs, the fragments are typically maintained in a gas phase and flowed over a nanowire or nanowire array, e.g., comprising functionalized nanowires for detection of a particular cellular target of interest. For example, a functional group on the nanowires is used to bind a component or fragment of interest, which binding event produces a signal in the nanowire, e.g., a change in conductance of the nanowire as described above. In some embodiments, a series of fragments is detected, e.g., to detect a pattern of markers, e.g., indicative of anthrax or some other biological warfare agent. In some embodiments, processing station 430 is included in the device, e.g., a filter or separation device, such as an HPLC, a mass spectrometer or a column filter. Other filtration and separation devices known to those of skill in the art are also optionally included in the device, e.g., coupled to the pyrolysis chamber and to the nanowire array. As shown in FIG. 4, processing station 430 is coupled to pyrolysis chamber 410 and to nanowire array 440. Furthermore, the nanosensor typically comprises a plurality of nanowires, e.g., each connected to a pair of electrodes, and a detector, e.g., an electrical detector which monitors a change in conductance of the nanowire, which conductance changes when one or more components binds to a nanowire and alters the local electrical field around the nanowire.

D. Analyte Detection at Multiple Concentrations

Figure 7:
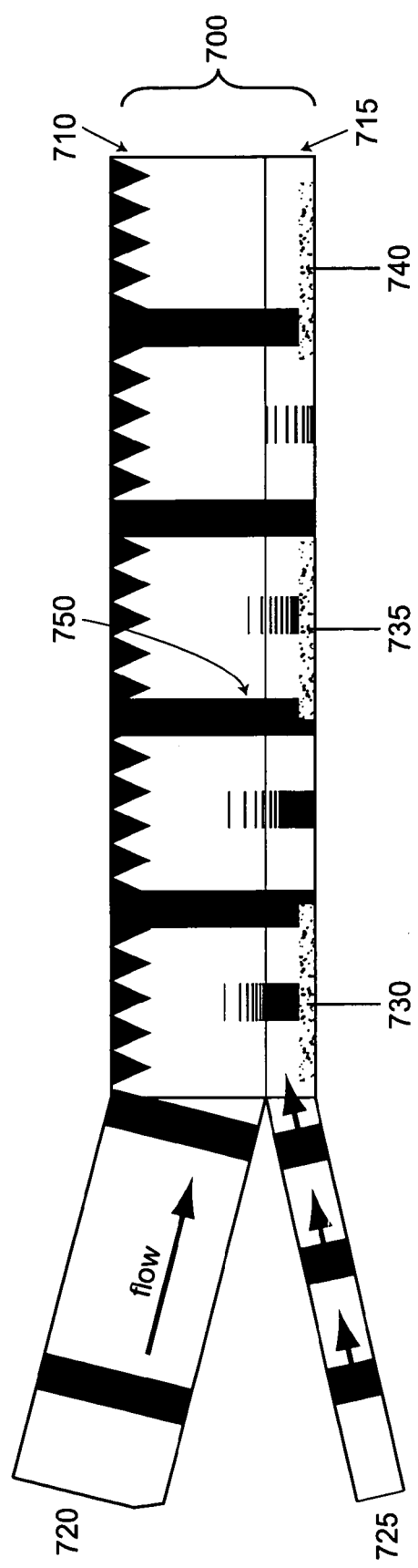
FIG. 7 provides a schematic illustration of an array of nanowires in a microchannel, e.g., for detection of an analyte at multiple concentrations, simultaneously.

In another embodiment, the present invention provides methods and devices for the simultaneous detection of an analyte at multiple concentrations, e.g., in a single assay. For example, the methods typically comprise flowing a buffer solution along the top of a microfluidic channel and flowing a test solution comprising the analyte along the bottom of the channel. The two solutions mix, resulting in a concentration gradient of the analyte along the bottom of the channel. As used herein, "concentration gradient" refers to a variation, e.g., a gradual variation, in the concentration of an analyte in a channel. For example, FIG. 7 illustrates a concentration gradient along a channel. The gradient typically forms as the solutions flow through the channel, gradually mixing along the way, thereby providing dilution of the analyte as a function of distance traveled. To detect the analyte at various concentrations along the gradient, an array of nanowires is typically positioned along the bottom of the channel. For example, FIG. 7 illustrates a nanowire array positioned along bottom surface 715 of channel 700. The nanowire array pictured comprises three distinct capture regions, e.g., capture regions 730, 735, and 740. As described above, the nanowires are optionally used to detect a binding event. The nanowires bind the analyte along the bottom of the channels, allowing detection of the analyte at various concentrations, e.g., at various positions along the bottom of the channel. An array is typically configured or positioned to detect analyte in at least two positions, typically at least about 3, or at least about 5 or more positions along the bottom of the channel. For example, one or more nanowires is placed in 3 different locations along the bottom of the microchannel. Detection at each of the nanowire positions is optionally used to provide detection of the analyte at the various concentrations along the gradient.

Specifically, the above invention is optionally used to provide a concentration dependent study of the effect of a test compound, e.g., an analyte on living cells, which are associated with or linked to the nanowires on the bottom of the channel.

Devices for detection of multiple concentrations are also provided. For example, a microchannel, groove, trench or the like, is typically provided. For example microfluidic devices are commercially available, e.g., a LabChip® as provided by Caliper Technolgies Corp. A microfluidic device typically has one or more microchannels, e.g., having one or more dimension that is less than 500 µm, or grooves disposed therein. For the present invention, at least one channel typically has a rough top surface, e.g., to aid mixing of components. For example, grooves are optionally etched in the top surface of a channel or an additional material that does not provide an even coat is added to the surface of the channel. The roughened surface is used to aid mixing of the two components that are typically flowed through the channel. In addition, the devices of the present invention comprise nanowires positioned in the microchannel. For example, multiple arrays of nanowires are optionally positioned at multiple positions, e.g., along the bottom of the channel.

FIG. 7 provides a schematic illustration of a channel of the invention. The methods and device are described below in relation to the figure. Channel 700 is a microchannel comprising rough top surface 710 and bottom surface 715. Two input channels are also typically provided. Input channel 720 delivers fluid to the top of channel 700 and input channel 725 delivers fluid to the bottom of channel 700. As the two fluids flow into channel 700, they typically mix, e.g., assisted by the rough top surface 710, which provides chaotic mixing. As the solutions mix, the analyte flowing through input tube 725 and diffuses into buffer solution flowing in through input tube 720, thus diluting the concentration of analyte flowing along bottom surface 715. Bottom surface 715 typically has multiple assay capture regions, e.g., capture regions 730, 735, and 740, disposed thereon or therein. The capture regions typically comprise one or more functionalized nanowires. The nanowires are typically functionalized with a binding moiety, e.g., that specifically binds to a component of interest. As the sample solution diffuses into the buffer solution, it flows through the channel, and contacts each of the assay capture regions. Therefore, when buffer is added on the top and analyte on the bottom, the first assay capture region experiences the highest concentration of analyte, e.g., capture region 730. Capture region 740 would then experience the lowest concentration of analyte and capture region 735 a middle range concentration. The order is optionally reversed by flowing the buffer in on the bottom of the channel and the analyte or sample solution in from the top. Additional capture regions are also optionally included. For example the channel optionally includes about 2 to about 20 capture regions, more typically about 3 to about 10. Because the nanowires produce a signal when an analyte binds to a binding moiety associated with the nanowire, only those components near the bottom of the channel are detected. Alternatively, the nanowires are positioned along the top of the channel. As illustrated in FIG. 7, some sample plugs are optionally flowed through the system without dilution, e.g., to serve as standards. For example, sample plug 750 flows through the channel undiluted because instead of buffer, a complementary sample plug is flowed through input channel 720 and intersects a like sample plug flowing in from input channel 725. The methods described above extend the dynamic range of the nanowire detection from detection of single binding events to arbitrarily high concentrations.

III. Detection of a Cellular Event or Cellular Response

In addition to detection of components of interest, the devices of the invention are also optionally used for cellular analysis, e.g., to measure cellular metabolism, cell viability, cell growth, cell death, cell migration, membrane potentials, and/or the like. Cells in the invention are optionally bacterial cells, animal cells, plant cells, spores, viral particles and the like. Typically, cells are derived from, e.g., a tissue sample, a blood sample, a cell lysate, cultured cells, and/or the like. A nanowire in close contact with a cell exhibits a change in conductance that is detectable. Although the cell is typically in close contact with the nanowire, a direct connection, e.g., a bond or other physical link, is not required for detection. The nearness of the cell itself produces a signal. Therefore, the nanowire is able to sense when a cell is nearby or when a cell has migrated away from or disassociated from the nanowire.

A "cellular response" or "cellular event" is used herein to refer to any response, e.g., reaction or change, a cell or other biological agent exhibits when exposed to a test compound, change in condition, or the like. For example, a cellular response typically takes the form of a new activity or inhibition of previous activity in an organism or any of its parts resulting from stimulation, e.g., by a test compound or change in environment. Examples include change in ion concentrations, change in membrane potentials, cell death, cell migration, cell proliferation, a morphological change, change in shape, or the like.

Improved detection of cellular responses is provided by the devices of the present invention. For example, a spatial array of nanowires is optionally used to simultaneously test for cell death, cell proliferation, and cell migration. The nanowires act as field effect transistors to detect the presence or absence of cells, e.g., either through specific or non-specific interaction of the cells with the nanowires. The nanowires serve as FETs that exhibit a change in conductance when a cell is proximal to or attached to the nanowire. Therefore, an array of nanowires is optionally used to monitor the attachment and detachment of cells from the array, thereby monitoring cell death, cell proliferation, and cell migration, e.g., simultaneously.

In one embodiment, the present invention provides real time monitoring of cellular transport, e.g., in intracellular communication, using nanowires or nanowire arrays. A nanowire or a nanowire array is prepared, e.g., in a microwell array by positioning one or more nanowire at the bottom of each well. The nanowires are optionally functionalized, e.g., each nanowire in the array is optionally individually addressed for parallel detection of a plurality of different analytes. Alternatively, the nanowires are non-functionalized nanowires. Cells are then typically distributed to each microwell, e.g., a single cell in each microwell wherein each cell associates with an individual nanowire. The cells are then typically contacted with a test compound, e.g., a drug candidate, a virus, a bacterium or the like. The nanowires are then used to detect any changes the cell undergoes as a result of the test compound.

The methods provided are optionally used to perform combinatorial drug screening. For example, a few tumor cells are optionally distributed to each microwell, e.g., in a 10 by 10 array. A different drug candidate, e.g., in the same amount, is distributed to each well. The effect of the drug candidate on the tumor cells is measured by a plurality of nanowires on the bottom of each well. For example, the nanowires are functionalized with specific receptors for one or more tumor growth factors produced when the tumor is proliferating. Other uses of the above system and methods include, but are not limited to, the study of a cellular response to a virus or bacterium, a cellular response to a toxin, and cellular metabolism.

Systems for performing the above screening are also provided herein. For example, a system optionally comprises a microwell array comprising nanowires, e.g., individually functionalized nanowires, at the bottom or side of each microwell. The system also typically includes a mechanism for distributing cells to the microwells, e.g., a pipet system, and for distributing the test compound, e.g., a drug candidate. In addition the system typically includes a mechanism to monitor physical changes of the cells in the microwell and to detect and interpret electrical changes in the nanowires, e.g., induced by chemical changes in the cells or by a binding event on the nanowire. For example, the nanowires are typically coupled to two electrodes and a electrical or digital detector. Specific nanosensor systems and assays are described in more detail below.

A. Detection of Cellular Responses

A surface comprising a plurality of nanosensors is optionally used to monitor several major cellular responses simultaneously as described below. For example, cell migration, cell death, cell proliferation, and morphological changes are optionally monitored simultaneously in the devices of the invention.

For example, a nanowire array with cells adhered thereto exhibits a signal due to the contact of the cells. When cell death occurs, the cells typically round up and detach from the surface of the nanowire. The signal is lost, the loss providing an indication of the cell death, e.g., in response to a test compound that was mixed with the cells on the nanowire array. If cells proliferate, they divide and grow, e.g., outward from the initial seeding point. As a result, after an appropriate period of time, the initial contacts are still there as well as additional contacts from the new cells. Morphological changes, e.g., neurite growth, cell spreading, and the like are also detectable in this manner. Cell migration is detectable because the initial adhesive contacts are lost and new contacts are made as the cells migrate to a new location on the array and adhere to that portion of the array. Therefore, a nanowire array in which cell migration had occurred would lose initial contacts, but gain new contacts, e.g., while the total amount of signal remains the same.

Cell migration refers to translation or movement of cells. For example, cell migration is exemplified by cell movement in developing embryos, movement of macrophages to injured tissues, retraction of blood clots by platelets exemplify the variety of cell motility. In the present invention, such movement would cause the cell to dissociate from one nanowire and associate with a different nanowire, e.g., a neighboring nanowire.

Figure 3:
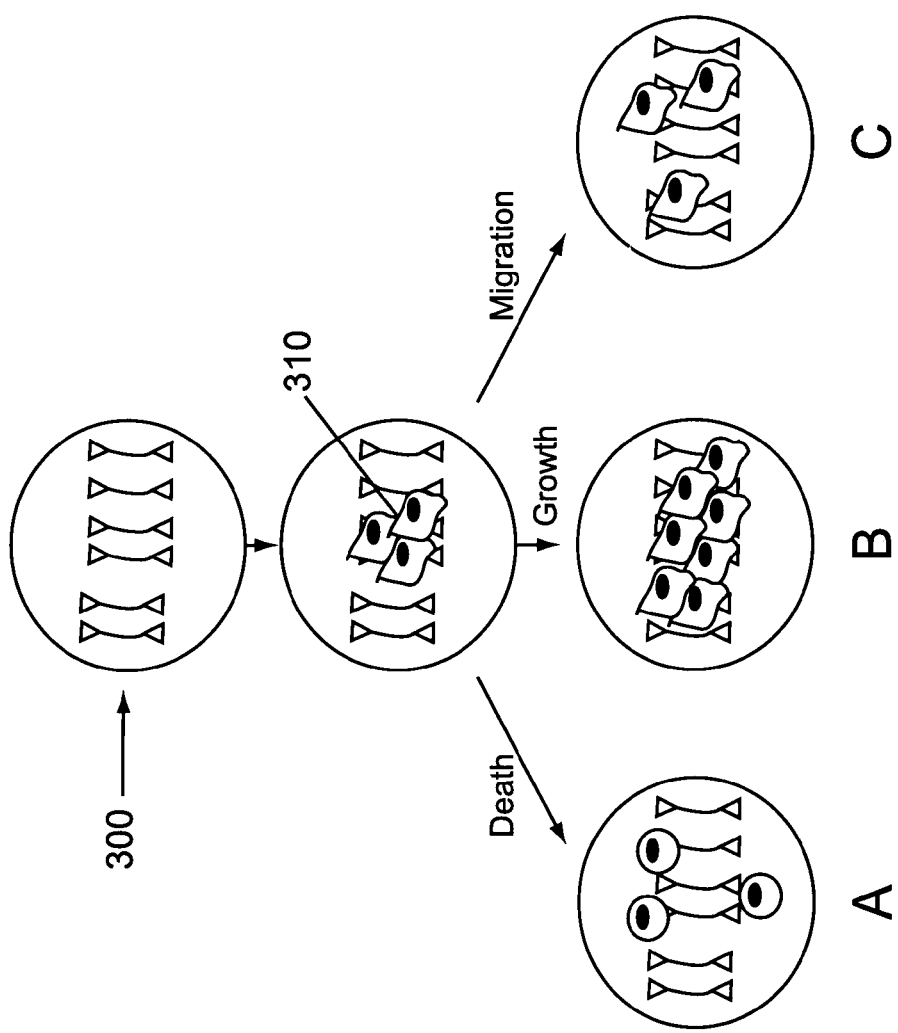
FIG. 3 illustrates how a nanowire array is used to simultaneously measure cell death, cell growth, and cell migration.

FIG. 3 illustrates a method by which multiple cellular responses are simultaneously monitored. A plurality of cells are added to nanowire array 300, e.g., comprising a plurality of electrically contacted nanowires, e.g., in a defined area, and allowed to adhere to or otherwise associate with nanowire array 300. As shown, cells 310 adhere to nanowire array 300, thereby generating a signal in the nanowires. When cell death occurs, as shown in Panel A, cells 310 lose contact with array 300 and the signal generated from nanowire array 300 due to the contact with the cells is lost. Panel B illustrates cell proliferation, in which cells 310 maintain contact and additional contacts are detected, by increased signal from nanowire array 300. Panel C illustrates the detection of cell migration. Original contacts for cells 310 are lost and new ones are added, indicating that the cells have not died, but have migrated. Growth of the cells indicates proliferation or morphological changes sufficient to make new contacts.

Nanowire arrays for use in the above methods typically involve a plurality of nanowires, e.g., functionalized with specific adhesion molecules, a portion of which are initially contacted with the cells to be analyzed and a portion of which are not initially contacted, e.g., leaving room on the array to detect migration and growth by additional cellular adhesion. The nanowires are optionally functionalized or non-functionalized. For example the surfaces of the nanowires are optionally modified to promote cellular adhesion, e.g., specific or non-specific, or left as an unmodified wires that are simply coated with silicon dioxide. As described above, cells are capable of detectably associating with a non-functionalized nanowire, even without a direct physical link.

The above methods are optionally used to test cell viabiltiy, e.g., in response to a pathogen, drug, toxin, or the like. For example, a cell is exposed to a drug and then simultaneously monitored for cell death, cell proliferation, and cell migration, to determine the effect of the drug on the viability of the cell.

B. Detection of Membrane Potentials

Intracellular monitoring and detection are also provided in the present invention. Nanowires provide a unique opportunity to assay cellular response, e.g., to external stimuli, from the inside of a cell. For example, a nanowire about 10 nm in diameter, e.g., smaller than a typical transmembrane protein, easily penetrates a cellular membrane without disrupting the membrane or harming or killing the cell. In fact, an appropriately treated nanowire surface is optionally used to induce the cell to engulf the nanowires, e.g., via endocytosis. An array of nanowires is optionally suspended such that one or more cells are optionally deposited thereon, e.g., to engulf the end of the nanowires. In this manner, an array of nanowires is created which is optionally used to assay changes in the cell interior. For, example, the nanowires are optionally used to measure analyte changes, e.g., changes in pH, changes in concentration of various ions, proteins, small molecules, and the like.

For example, intracellular detection methods provide nano-patch clamp arrays to measure cellular potential. Currently, patch clamp studies are performed by inserting an electrode through the cellular membrane and measuring the potential across the membrane. Traditional probes are large and typically result in cell death due to permanent damage to the cellular membrane. A small diameter, conducting nanowire provides a no-invasive or non-damaging patch clamp probe. The nano-patch clamp arrays are optionally formed by endocytosis as described above, and are optionally used to study a variety of cell types, e.g., by depositing a variety of cells on the array of nanowires and/or to study cellular response to a plurality of different stimuli. In addition to patch-clamp arrays, the intracellular nanowires are optionally used, e.g., to screen a cell, e.g., an embryonic cell, for disease, e.g., using a functionalized nanowire.

An alternate method of performing a nano-patch clamp assay is to insert the nanowire into a microwell comprising a cell or cells to be measured and providing a liquid-tight seal (a gigaohm seal") on the microwell. A gigaohm seal typically refers to a seal that ensures that current flowing through a nanowire or electrode inserted through a membrane, e.g., in a patch clamp assay, is substantially identical with current flowing through the membrane through which the nanowire or electrode is inserted. In the present methods, the gigaohm seal ensures that the current flowing through the nanowire in the microwell is substantially identical to the current flowing across the membrane of interest. The nanowire in this embodiment typically has no surface functionlization and although typical patch clamp studies measure the membrane potential by inserting an electrode into the cell and measuring the potential across the cell as different stimuli are added to the cell, the methods provided herein measure changes in membrane potential on the outside of the cell. The nanowires is in a confined space, e.g., in the microwell and underneath the cell typically. As the potential changes on the inside of the cell, an equal change is seen o the outside since the change results from ions traveling from one side of the membrane to the other. The exterior potential is optionally measured with a nanowire.

C. Multi-Element Detection

Various elements described above are optionally combined to provide multi-element nanosensors, e.g., integrated into a microfluidic system. For example, two types of nanowire detectors are optionally combined in a microfluidic system to provide multi-element detection. The first nanowire detector typically detects the presence of an analyte, e.g., by binding an analyte to a binding moiety affixed to the nanowire, such as a capture antibody or phage. For example, an antibody or phage is optionally used to directly bind an analyte of interest, thus providing a direct measure of the presence of the analyte in a sample solution from the change in conductance of the nanowire upon binding. The second type of detection is optionally a nano-physiometry detector that measures changes in local pH, e.g., resulting from a change in the metabolism of living cells. This is also measured as a change in conductance of the nanowire. This system provides, e.g., detection of an analyte in combination with detection of cell viability.

FIGS. 9A, 9B, and 9C provide a schematic illustrating two detection elements that are optionally combined into a single assay and device. FIG. 9A illustrates nanowire 910 comprising binding moieties 920, e.g., phage capture elements that would be used in a first stage to detect the presence of a component of interest. FIG. 9B illustrates as second detection element, e.g., nanowire 930 comprising amine functional groups 940 for detecting a change in pH. FIG. 9C illustrates a microfluidic channel with nanowires arrayed therein. For example, the wires are optionally positioned such that wires 910 and 930 are alternating along the channel. Sheath flow of fluids through the channel, e.g., flow that is constrained laterally by concurrent flowing streams, is used to focus the sample over the detector array.

For example, sample plugs are optionally flowed across a nanowire array, e.g., an assay capture field comprising functionalized nanowires in a microchannel. Any target organism, e.g., a cell, enzyme, bacterium, or the like, in the sample plug binds to the functional group on the nanowire, e.g., an antibody, phage, enzyme substrate, or the like, and produces a measurable signal in the nanowire to which it binds. For example, spores are optionally detected by binding to phage that have been linked to the nanowires, e.g., using cell immobilization techniques known to those of skill in the art. The density of wires arrayed on the surface of the channel is variable, e.g., it can be selected to optimize binding efficiency and minimize steric hindrance. As the sample plugs flow over the nanowires, e.g., the capture field, the target organism binds to the functional group on the wire, e.g., an antibody, phage, enzyme substrate, or the like. Each binding event produces a measurable signal in the nanowire, thus allowing the binding events to be counted directly from the number of discrete changes in conductance (even if the changes are not all of the same magnitude), e.g., over all the nanowires in the array. If landing and pinning by phage is faster than the time between landing events, the ratio of cells in the sample to the number of positive hits by the target sequence is optionally quantified. This measurement is optionally performed at multiple concentrations of sample as described above, e.g., to provide greater dynamic range in the detection of cells.

After the target molecule is detected, the array is typically washed, e.g., to remove any unbound cellular components. Wash fluids are typically buffers, e.g., at physiological pH, water, e.g., distilled water, and the like. In addition, the wash fluid optionally includes surfactants to minimize non-specific binding. If the signal from non-specific binding is too high during the binding phase, the signal due to binding may be measured in the presence of the buffer to minimize signal from the sample solution generally. Typically, cells are large enough that a binding event comprising a cell binding to a nanowire is typically detectable over noise, e.g., non-specific binding. The wash step typically prepares the channel and the array capture fields for the next step in the assay, e.g., viability analysis. For example, in assays having multiple stages, such as a detection and a physiometry stage, a wash step is typically used to increase sensitivity of the second stage.

Figure 10B:
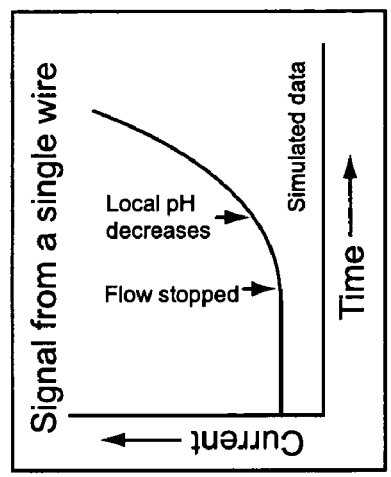
FIG. 10B provides simulated data for a cell viability assay as shown in FIG. 10A.
Figure 10A:
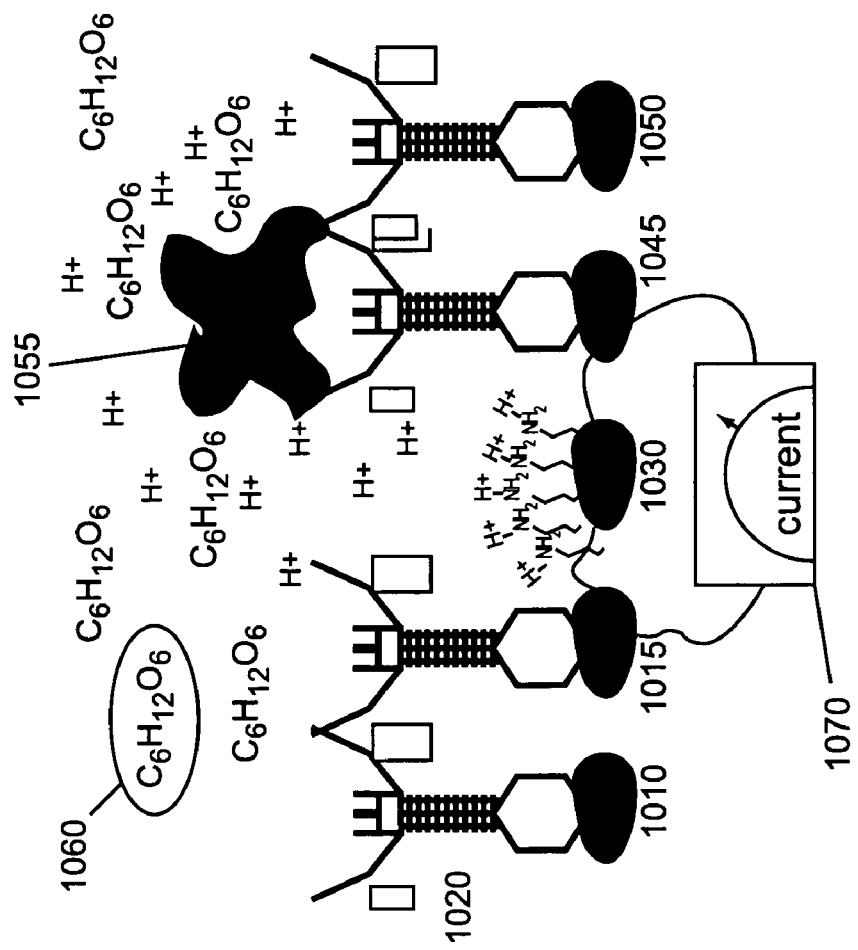
FIG. 10A provides a schematic illustration of a cell viability assay using a nanowire array.

For example, a second stage is optionally used to test cell viability. An example of cell viability testing is illustrated by FIGS. 10A and 10B. A glucose solution is optionally flowed through the channel to test cell viability. Typically, the glucose solution is flowed across the cells without a concentration gradient such that all captured cells experience the same glucose concentration. However, the concentration of glucose can also be varied as described above. Typically, the glucose solution is allowed to incubate with the captured cells, e.g., by stopping the flow of the solution trough the channel when it is in contact with an assay capture region, e.g., a capture region comprising one or more captured cells or spores. At this point a second set of nanowires, e.g., non-functionalized nanowires, is typically used to measure the cell viability. The second set of nanowires monitors the solution, e.g., the pH, with which they are in contact. FIG. 10A illustrates an arrangement of nanowires in which nanowires 1010, 1015, 1045 and 1050 are used to capture cells, e.g., cell 1055 on binding moiety 1020, and nanowire 1030, an amine functionalized nanowire, is used to detect a change in pH when cell 1055 metabolizes glucose molecules 1060, thereby increasing the concentration of H$^+$ in solution. The change is detected on current meter 1070. viable cells metabolize glucose and produce a change in local pH over time. This change is detected as a change in current in the nanowire over time as illustrated by the simulated data pictured in FIG. 10B. If a signal is produced due to the changing pH, then the cells are typically considered viable. If multiple binding events have been detected, and no change in pH is detected, the cells are typically not viable. The relative number of viable organisms in the sample is optionally obtained from the relation between the number of binding events and the increase in pH. Nanophysiometry is also optionally used to test the viability of captured spores because viable spores also have detectable metabolic activity.

In other embodiments, infection of a cell, e.g., by a virus is monitored. For example, viral DNA infecting a cell results in increased metabolism. In addition, viral DNA is optionally engineered to deliver a gene that further increases metabolism for enhanced differentiation. Alternatively, the cell is optionally infected with a gene that encodes a protein that is expelled from the cell. Specifically functionalized nanowires are optionally used to detect the product of the infection or to detect the increased metabolism. For example, vesicular stomtitus virus or HIV can cause a decrease in pH, which is detectable, e.g., with the nanowires of the invention as described above. For more on cellular metabolism and physiometry, see, e.g., Parce et al., (1989) *Science* 246:244. See also, Molecular Biology of the Cell, second edition, by Alberts et al., 1989 (Garland Publishing, New York), for more information on cellular metabolism.

In other embodiments, the presence of an enzyme and its activity are optionally assayed in the same manner as described above. For example, a phosphatase is optionally detected by binding to a phosphatase substrate and then tested for activity by monitoring a change in charge of the substrate.

Figure 12:
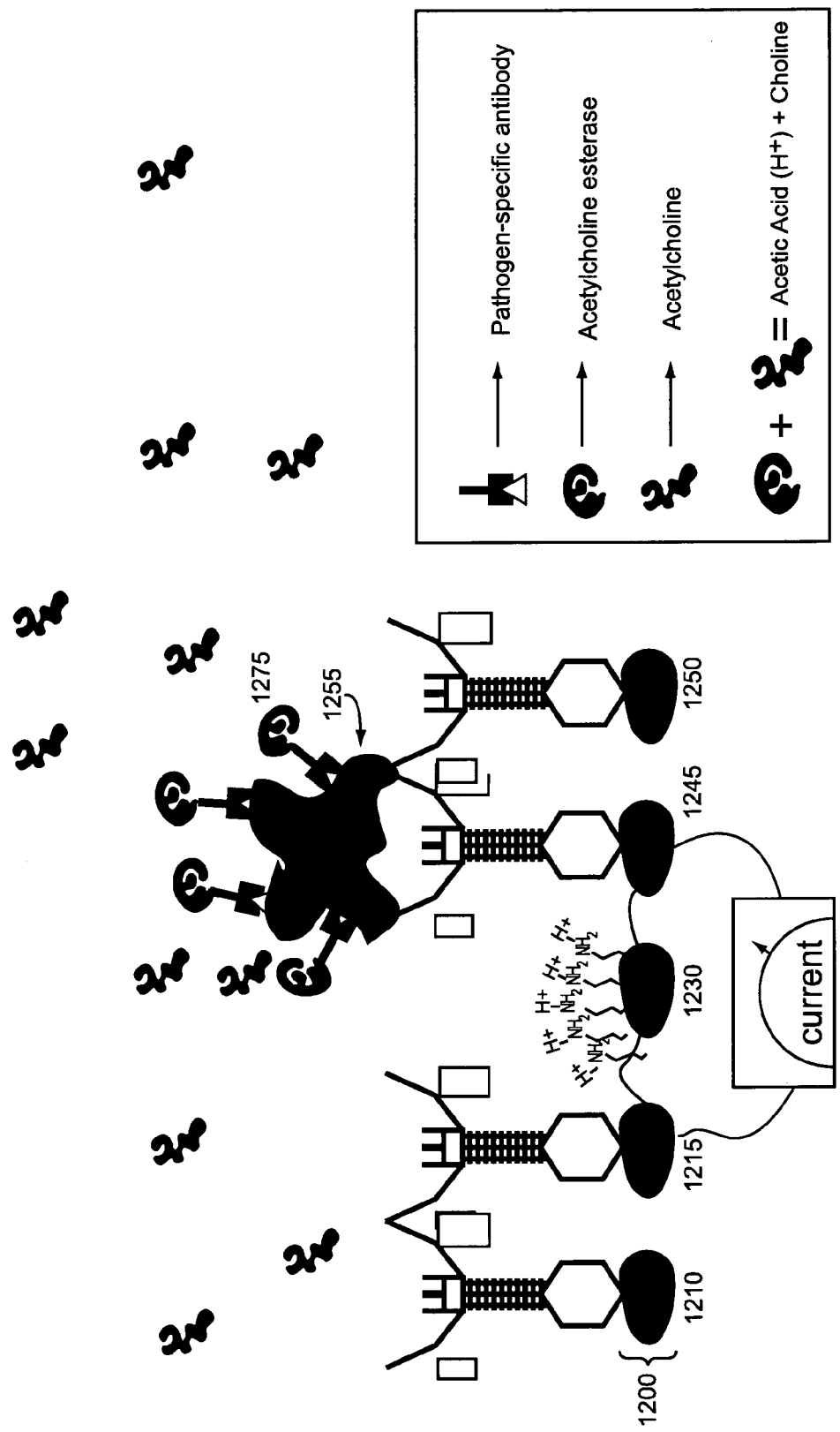
FIG. 12 illustrates secondary detection of cells using a nanowire.

In some embodiments, the methods of the invention include the ability to assess an assay for false positives. For example, a labeling step is optionally included in any of the assays described herein, e.g., at the end of the assay. For example, acetylcholine esterase-labeled antibodies are optionally flowed across captured cells, e.g., a homogeneous solution as opposed to a concentration gradient. The antibodies are typically selected to be specific for a different element or epitope of the organism than what was recognized on the capture field to bind the organism in the first step. If the cell or organism contains the second epitope, the enzyme is bound to the cell, after which acetylcholine is added to the capture field and allowed to incubate, e.g., by temporarily stopping fluid flow in a channel. The enzyme processes the acetylcholine and produces a change in pH that is detected as described above. FIG. 12 illustrates secondary detection as described above. For example, nanowire array 1200 comprises functionalized nanowires 1210, 1215, 1245, and 1250 and amine-functionalized nanowire 1230 for detecting pH. In this example, cell 1255 comprises enzyme-labeled pathogen specific antibodies 1275, e.g., labeled with acetylcholine esterase. When the acetylcholine esterase binds to acetylcholine, the resulting reaction that alters the local pH. The change in pH at this stage provides an indication of the presence of both epitopes on the captured cells or spores. The ratio of capture events to pH change is optionally used to assess the possibility of false positives in the capture stage or is optionally used to confirm capture of non-viable cells that produce no signal in the physiometry stage of the assay. Any antibody linked enzyme is optionally used for this step other than acetylcholine esterase, wherein the output of the enzymatic reaction can be linked to a specific detectable event, such as a change in pH or a binding event that can be detected using an additional set of wires, other than those used as the capture nanowires.

Alternatively, the secondary labeling is used as an amplification system, e.g., if a change in pH due to metabolism is too low to be monitored, as a verification test for the presence of the cells of interest.

Figure 13:
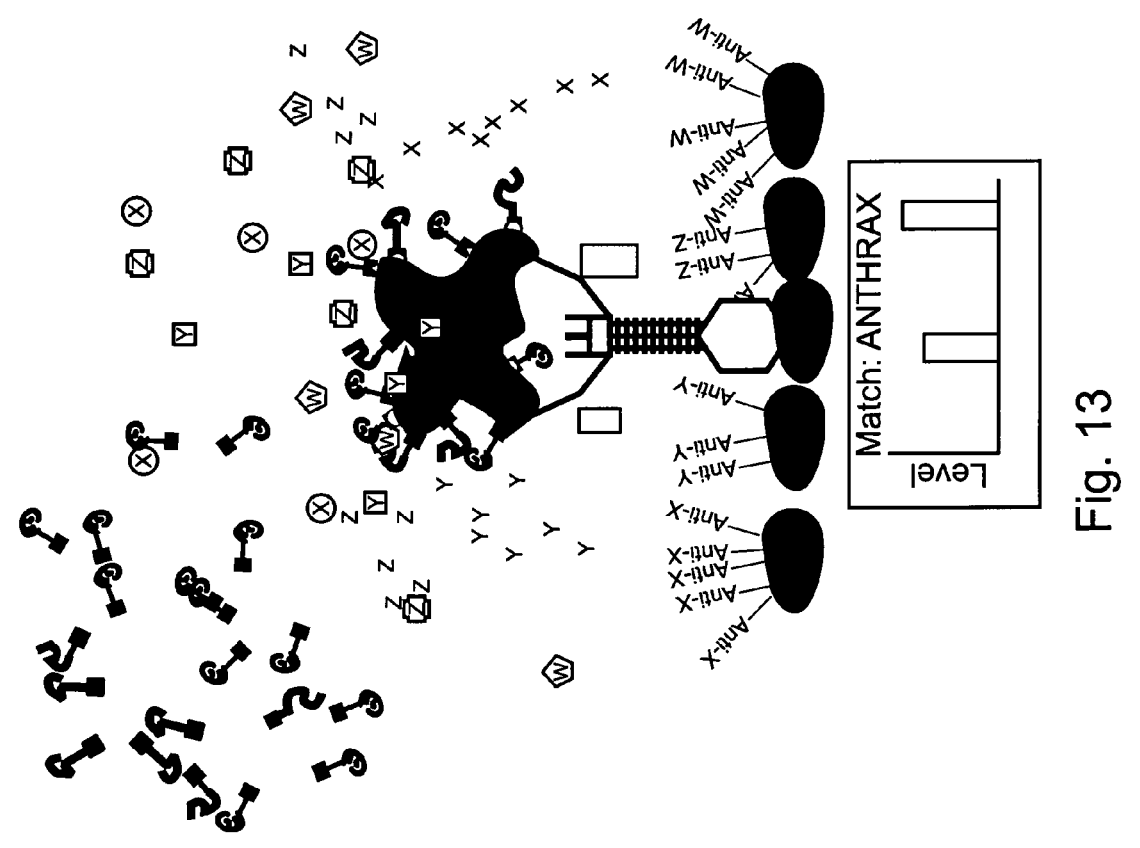

FIG. 13 illustrates another embodiment of the invention wherein a plurality of different enzyme/substrate/product combinations are used simultaneously to provide high specificity discrimination, e.g., a bacterial fingerprint. Each enzyme is attached to a different antibody for a surface epitope of a cell, e.g., of a pathogen. A plurality of nanowires is provide wherein nanowires are provided that specifically bind to the product of each enzyme included in the assay. The nanowires then detect enzyme activity for each enzyme, wherein the local concentration of each product depends on the level of expression of each epitope on the cell surface. The levels of expression are then optionally compared to various standards to identify the captured cell or pathogen, e.g., anthrax.

IV. Kits

Nanosensor kits typically include a plurality of nanowires, e.g., arrayed on a substrate such as a microwell or microchannel. The kits are typically provided with nanowires positioned within a microfluidic channel or microwell, e.g., functionalized or non-functionalized nanowires. Generally, the nanosensors and nanosensor arrays described herein are optionally packaged to include reagents for performing one or more preferred function. For example, the kits optionally include a microfluidic device or microwell plate as described along with assay components, reagents, functional groups, sample materials, and/or the like. For example a glucose assay kit typically includes one or more nanowires, e.g., an array of nanowires with glucose oxidase linked thereto, or a group of reagents for linking glucose oxidase to a nanowire array. Kits also typically include appropriate instructions for using the devices and reagents, and in cases where the nanowires are not functionalized, reagents and instructions for preparing functionalized nanowires. Kits also optionally include additional devices for introducing materials onto the nanowire arrays, e.g., appropriately configured syringes/pumps/pipettes, and the like.

It is to be understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting a component of interest, the method comprising:
   (a) providing one or more nanowires, which nanowires comprise one or more functional groups comprising a hairpin oligonucleotide, which functional group undergoes a change in charge in the presence of the component of interest, wherein the hairpin comprises a first end, a second end, and a central portion, wherein the first end and the second end are complementary to each other and the central portion is complementary to the component of interest, and wherein the first end comprises a charge moiety that is proximal to the nanowires;
   (b) contacting the one or more nanowires with a solution comprising the component of interest; wherein binding the component of interest to the central portion of the hairpin oligonucleotide unfolds the hairpin, thereby moving the charge moiety away from the nanowires, producing the change in charge which change in charge results in a detectable signal; and,
   (c) detecting the signal, thereby detecting the component of interest.

2. The method of claim 1, wherein the component of interest comprises an enzyme, a nucleic acid, or a protein.

3. The method of claim 1, wherein the charge moiety comprises a latex bead comprising a carboxylate or amine surface, a nucleic acid, a highly charged polypeptide, a charged polymer, one or more negatively charged nucleotides, or a metal nanocrystal.

4. The method of claim 1, wherein the one or more nanowires comprise a nanowire array.

5. The method of claim 1, wherein the one or more nanowires are positioned in one or more microwells or within a microfluidic device.

6. The method of claim 1, wherein the component of interest comprises a cellular component.

7. The method of claim 1, wherein the change in charge comprises a redistribution of charge.

8. The method of claim 1, wherein the solution comprises one or more cells, one or more cellular fragments, a tissue sample, a cell lysate, or a blood sample.

* * * * *